(12) United States Patent
Lee et al.

(10) Patent No.: US 6,492,402 B1
(45) Date of Patent: Dec. 10, 2002

(54) THROMBIN INHIBITORS

(75) Inventors: Koo Lee, Yusong-gu (KR); Won Hyuk Jung, Ansan-si (KR); Cheol Won Park, Seodaemun-gu (KR); Sang Koo Lee, Yusong-gu (KR); Sun Hwa Lee, Yusong-gu (KR); Hee Dong Park, Seo-gu (KR)

(73) Assignee: LG Life Sciences, Ltd., Taejon (KR)

( * ) Notice: Subject to any disclaimer, the term of this patent is extended or adjusted under 35 U.S.C. 154(b) by 0 days.

(21) Appl. No.: 09/473,681

(22) Filed: Dec. 29, 1999

(30) Foreign Application Priority Data

Dec. 29, 1998 (KR) ............................................. 98-60266
Aug. 14, 1999 (KR) ............................................. 99-33490

(51) Int. Cl.⁷ .................... C07D 409/12; C07D 403/12; C07D 417/12; C07D 407/12; A61P 9/10
(52) U.S. Cl. ...................... 514/365; 514/374; 514/378; 514/406; 514/422; 548/204; 548/236; 548/247; 548/364.1; 548/517; 548/523; 548/527
(58) Field of Search ................................ 514/365, 378, 514/374, 422, 406; 548/204, 236, 247, 223, 227, 364.1, 517

(56) References Cited

U.S. PATENT DOCUMENTS

| | | | |
|---|---|---|---|
| 5,705,487 A | * 1/1998 | Schacht et al. | 514/19 |
| 5,914,319 A | 6/1999 | Schacht et al. | 514/19 |
| 5,932,567 A | 8/1999 | Seitz et al. | 514/210 |

FOREIGN PATENT DOCUMENTS

| | | | |
|---|---|---|---|
| WO | WO 99/37611 | * | 1/1999 |
| WO | WO 99/37668 | * | 1/1999 |

* cited by examiner

*Primary Examiner*—Richard L. Raymond
*Assistant Examiner*—Thomas C McKenzie
(74) *Attorney, Agent, or Firm*—Shanks & Herbert

(57) ABSTRACT

The present invention relates to a compound having formula I:

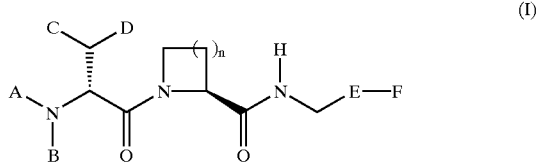

and pharmaceutically acceptable salts thereof. The compounds of formula I and pharmaceutical compositions containing them are of the class of thrombin inhibitors which are useful as anticoagulants.

16 Claims, No Drawings

THROMBIN INHIBITORS

FOREIGN PRIORITY CLAIM

This application claims priority under 35 U.S.C. §119 to Korean patent applications KR 1998-0060266 filed Dec. 29, 1998 and KR 1999-0033490 filed Aug. 14, 1999.

FIELD OF THE INVENTION

The present invention relates to thrombin inhibitors that are useful as anticoagulants. In particular, this invention relates to peptide derivatives having high antithrombotic activity and high oral bioavailability.

BACKGROUND OF THE INVENTION

Thrombosis is characterized by excessive blood clotting. The condition plays a significant role in cardiovascular and related diseases, and thrombotic events underlie a significant proportion of the mortality and morbidity associated with cardiovascular disease. Thrombosis can cause a range of disease states which are characterized by the location of the blood vessel in which the clot is formed.

Thrombin is a trypsin-like serine protease that plays a key role in the blood coagulation cascade by catalyzing the conversion of fibrinogen to insoluble fibrin. This enzyme also activates Factor V and Factor VIII for its own production and potently activates platelets as well. Therefore, thrombin has long been recognized as a central regulator in thrombosis and hemostasis, and its inhibition has become a major therapeutic target in the treatment of cardiovascular diseases such as myocardial infarction, unstable angina, deep vein thrombosis and pulmonary embolism. Indirect thrombin inhibitors such as heparin and warfarin (coumarin) have been used as antithrombotic therapies with, however, several limitations. Heparin demonstrates low bioavailability and is associated with side effects such as bleeding problems, moreover, it is not able to inhibit clot-bound thrombin. Warfarin is an effective oral anticoagulant but it has a narrow therapeutic window and also requires patient monitoring. A natural protein inhibitor, hirudin, has been associated with bleeding complications.

Most of the low molecular weight thrombin inhibitors are broadly based upon peptides or peptidomimetic templates which operate by a direct mechanism of action against the target enzyme. Early examples are tripeptidic aldehydes such as D-Phe-Pro-Arg-H and Me-D-Phe-Pro-Arg-H that have been reported to be effective thrombin inhibitors (Bajusz et al. J. Med. Chem. 1990, 33, 1729).

Recently, D-Phe-Pro-Agmatine and its derivatives have been described as thrombin inhibitors in U.S. Pat. No. 4,346,078 and WO93/11152 (agmatine=1-amino-4-guanidinobutane). These compounds are different from the earlier tripeptidic compounds in that the agimatine compounds lack a carbonyl moiety found in similar compounds containing an Arg side chain.

More recently, certain tripeptidic thrombin inhibitors in which 4-amidinobenzylamaine was incorporated at the P1 position in place of agmatine have been disclosed (WO 94/29336). These amidine-based compounds have been reported to possess good antithrombotic activity (WO 95/23609). However, this class of compounds has generally poor or low oral bioavailability.

Certain thrombin inhibitors bearing the unique amino acid D-diphenylalanine at P3 position have been disclosed (WO 93/11152, U.S. Pat. No. 5,510,369, WO 97/15190). These compounds have been reported to have higher potency against thrombin compared to the corresponding D-phenylalanine alalogs (J. Med. Chem. 1992, 35, 3365; J. Med. Chem. 1997, 40, 830). In addition, some of this class of compounds exhibited good oral bioavailability (J. Med. Chem. 1997, 40, 3687; J. Med. Chem. 1997, 40, 3726).

In certain thrombin inhibitors and Factor Xa inhibitors, the amidinothiophene groups have been shown to be better para-benzamidine surrogates (WO 95/23609, WO98/24784, Bioorg. Med. Chem. Lett. 1998, 8,1683). In addition, 2,5-thiophene and other 5-membered heterocyclic moieties have effectively served as a para-phenylene isostere in the inhibitors of other drug-targeting enzymes such as thymidylate synthase and glycinamide riobonuceotide formyltransferase (J. Med. Chem. 1991, 34, 1594; Cancer Research 1994, 54,1021; WO 97/41115).

Therefore, there is a need in the art for thrombin inhibitors which have improved oral bioavailability and stablility as compared to those described supra. We have found that the compounds of the present invention, as defined below, are potent inhibitors of thrombin in vitro and in vivo. In particular, certain compounds of this invention exhibit high bioavailability after oral administration.

SUMMARY OF THE INVENTION

The present invention relates to compounds falling within formula I below which modulate and/or inhibit the serine protease thrombin, as well as to acceptable prodrugs, pharmaceutically active metabolites, and pharmaceutically acceptable salts thereof (such compounds, prodrugs, metabolites and salts are collectively referred to as "agents"). The invention is also directed to pharmaceutical compositions containing such agents and their therapeutic use in treating diseases mediated by thrombin, such as myocardial infarction, unstable angina, deep vein thrombosis and pulmonary embolism, as well as other disease states associated with blood clotting and associated clotting factors.

In one general aspect, the invention relates to thrombin inhibitors of the Formula I:

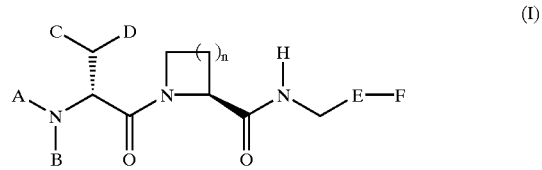

and pharmaceutically acceptable salts thereof
wherein:
n is 1, 2, or 3,
A is hydrogen, alky, $C_{3-7}$ cycloalkyl, aryl, —$SO_2R^1$, —$SO_3R^1$, —$COR^1$, —$CO_2R^2$, —$PO(R^1)_2$, —$PO(OR^1)_2$, —$(CH_2)_mCO_2R^1$, $(CH_2)_mSO_2R^1$, —$(CH_2)_mSO_3R^1$, or —$(CH_2)_mPO(OR^1)_2$,
wherein:
$R^1$ is hydrogen, $C_{1-6}$ alkyl, $C_{3-7}$ cycloalkyl, aryl, —$(CH_2)_m$aryl, or —$NR^3R^4$, and
$R^2$ is $C_{1-6}$ alkyl, $C_{3-7}$ cycloalkyl, aryl, —$(CH_2)_m$aryl, or alkenyl,
m is 1, 2, or 3,
wherein:
aryl is unsubsituted or substituted phenyl or 5–6 membered aromatic heterocyclic ring,
$R^3$ and $R^4$ are independently hydrogen, $C_{1-6}$ alkyl, or $C_{3-7}$ cycloalkyl;

B is hydrogen or $C_{1-6}$ alkyl;

C and D are independently hydrogen, unsubsituted or substituted phenyl with one or two substituents selected from $C_{1-4}$ alkyl, $C_{1-4}$ alkoxy, $CF_3$, methylenedioxy, halogen, hydroxy, or —$NR^3R^4$, $C_{3-7}$ cycloalkyl, or a 5–6 membered heterocyclic ring system which may be saturated or unsaturated, and which consists of carbon atoms and 1–3 heteroatoms selected from the group consisting of N, O, and S;

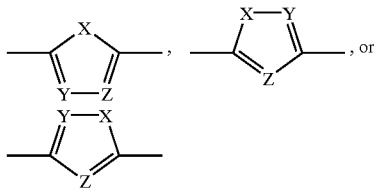

wherein
X is S, O, or $NR^5$,
Y and Z are independently N or $CR^6$,
wherein
$R^5$ is hydrogen or $C_{1-4}$ alkyl and
$R^6$ is hydrogen, halogen, $CF_3$ or $C_{1-4}$ alkyl; and
F is —$C(NH)N(R^7)_2$, —$C(NH_2)NN(R^7)_2$, —$C(NH_2)NOH$, or —$CH_2NH(R^7)_2$
wherein $R^7$ is the same or different,
$R^7$ is hydrogen, $C_{1-4}$ perfluoroalkyl or $C_{1-4}$ alkyl.

The invention also relates to pharmaceutical compositions each comprising: an effective amount of an agent selected from compounds of Formula I and pharmaceutically acceptable salts, pharmaceutically active metabolites, and pharmaceutically acceptable prodrugs thereof; and a pharmaceutically acceptable carrier or vehicle for such agent. The invention further provides methods of treating cardiovascular diseases such as myocardial infarction, unstable angina, deep vein thrombosis and pulmonary embolism, as well as other disease states associated with excess thrombin.

DETAILED DESCRIPTION OF THE INVENTION

The inventive compounds of Formula I are useful for mediating the activity of trypsin-like serine proteases. More particularly, the compounds are useful as anti-coagulant agents and as agents for modulating and/or inhibiting the activity of trypsin-like serine proteases, thus providing treatments for thrombosis and other cardiovascular diseases such as myocardial infarction, unstable angina, deep vein thrombosis and pulmonary embolism.

The terms and abbreviations used in the instant disclosure have their normal meanings unless otherwise designated.

As used in the present application, the following definitions apply:

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both stereoisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl, isopropyl, butyl (Bu), isobutyl, t-butyl (t-Bu), ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable susstituents as defined below (e.g., one or more halogens, such as F, Cl, Br, or I, with F and Cl being preferred).

A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents.

A "heterocycloalky group" is intended to mean a non-aromatic monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, which includes 1, 2, 3, 4, or 5 heteroatoms selected nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents.

An "aryl group" is intended to mean an aromatic monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl)., or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents.

A "heterocycle" is intended to mean a heteroaryl or heterocycloalkyl group (each of which, as defined above, are optionally substituted).

An "acyl group" is intended to mean a —C(O)—R radical, where R is a substituent as defined below.

A "thioacyl group" is intended to mean a —C(S)—R radical, where R is a substituent as defined below.

A "sulfonyl group" is intended to mean a —$SO_2R$ radical, where R is a substituent as defined below.

A "hydroxy group" is intended to mean the radical —OH.

An "amino group" is intended to mean the radical —$NH_2$.

An "alkylamino group" is intended to mean the radical —$NHR_a$, where $R_a$ is an alkyl group.

A "dialkylamino group" is intended to mean the radical —$NR_aR_b$, where $R_a$ and $R_b$ are each independently an alkyl group.

An "alkoxy group" is intended to mean the radical —$OR_a$, where $R_a$ is an alkyl group. Exemplary alkoxy groups include methoxy, ethoxy, propoxy, and the like.

An "alkoxycarbonyl group" is intended to mean the radical —C(O)OR$_a$, where R$_a$ is an alkyl group.

An "alkylsulfonyl group" is intended to mean the radical —SO$_2$R$_a$, where R$_a$ is an alkyl group.

An "alkylaminocarbonyl group" is intended to mean the radical —C(O)NHR$_a$, where R$_a$ is an alkyl group.

A "dialkylaminocarbonyl group" is intended to mean the radical —C(O)NR$_a$R$_b$, where R$_a$ and R$_b$ are each independently an alkyl group.

A "mercapto group" is intended to mean the radical —SH.

An "alkylthio group" is intended to mean the radical —SR$_a$, where R$_a$ is an alkyl group.

A "carboxy group" is intended to mean the radical —C(O)OH.

A "carbamoyl group" is intended to mean the radical —(O)NH$_2$.

An "aryloxy group" is intended to mean the radical —OR$_c$, where R$_c$ is an aryl group.

A "heteroaryloxy group" is intended to mean the radical —OR$_d$, where R$_d$ is a heteroaryl group.

An "arylthio group" is intended to mean the radical —SR$_c$, where R$_c$ is an aryl group.

A "heteroarylthio group" is intended to mean the radical —SR$_d$, where R$_d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

Typical protecting groups, reagents and solvents are well known in the art. One skilled in the art would know possible protecting groups, reagents and solvents; these are intended to be within the scope of this invention.

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

The term "substituent" or "suitable substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The terms "comprising" and "including" are used in an open, non-limiting sense.

A "pharmaceutically acceptable prodrug" is a compound that may be converted under physiological conditions or by solvolysis to the specified compound or to a pharmaceutically acceptable salt of such compound.

A "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

A "pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form pharmaceutically acceptable salt. Exemplary pharmaceutically acceptable salts include those salts prepared by reaction of the compounds of the present invention with a nimeral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycollates, tartrates, methanesulfonates, propanesulfonates, naphthalene-1-sulfonates, naphthalene-2-sulfonates, and mandelates.

Some abbreviations that appear in this application are as follows:
Boc: t-butoxycarbonyl
Pro: proline
EDC: 1-ethyl-3-(3-dimethylaminopropyl)carbodiimide hydrochloride
HOBT: 1-hydroxybenzonitrile hydrate
TFA: trifluoroacetic acid
AcOH: acetic acid
DMF: dimethylformamide
EtOAc: ethyl acetate
HCl: hydrochloride
rt: room temperature
TEA: triethylamine
FAB MS: fast atom bombardment mass spectrum If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid , such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Preferred compounds of the invention include, but are not limited to the following:

1. N-aminosulfonyl-D-diphenylalanyl-L-prolyl-[(5-amidino-2-thienyl)methyl]amide,
2. N-aminosulfonyl-D-diphenylalanyl-L-prolyl-[(5-aminomethyl-2-thienyl)methyl]amide,
3. N-methylsulfonyl-D-diphenylalanyl-L-prolyl-[(5-amidino-2-thienyl)methyl]amide,
4. N-methylsulfonyl-D-diphenylalanyl-L-prolyl-[(5-amidrazono-2-thienyl)methyl]amide,
5. N-methylsulfonyl-D-diphenylalanyl-L-prolyl-[(5-aminomethyl-2-thienyl)methyl]amide,
6. N-benzylsulfonyl-D-diphenylalanyl-L-prolyl-[(5-amidino-2-thienyl)methyl]amide,
7. N-t-butoxycarbonyl-D-diphenylalanyl-L-prolyl-[(5-amidino-2-thienyl)methyl]amide,
8. N-methoxycarbonyl-D-diphenylalanyl-L-prolyl-[(5-amidino-2-thienyl)methyl]amide,
9. N-aminosulfonyl-D-3,4-dichlorophenylalanyl-L-prolyl-[(5-amidino-2-thienyl)methyl]amide,
10. N-methoxycarbonyl-D-dicyclohexylalanyl-L-prolyl-[(5-amidino-2-thienyl)methyl]amide,
11. N-aminosulfonyl-D-diphenylalanyl-L-prolyl-[(4-amidino-2-thienyl)methyl]amide,
12. N-methylsulfonyl-D-diphenylalanyl-L-prolyl-[(4-amidino-2-thienyl)methyl]amide,
13. N-methylsulfonyl-D-diphenylalanyl-L-prolyl-[(4-aminomethyl-2-thienyl)methyl]amide,
14. N-methoxycarbonyl-D-diphenylalanyl-L-prolyl-[(4-amidino-2-thienyl)methyl]amide,
15. N-aminosulfonyl-D-diphenylalanyl-L-prolyl-[(5-amidino-3-thienyl)methyl]amide,
16. N-methylsulfonyl-D-diphenylalanyl-L-prolyl-[(5-amidino-3-thienyl)methyl]amide,
17. N-methylsulfonyl-D-diphenylalanyl-L-prolyl-[)5-amidrazono-3-thienyl)methyl]amide,
18. N-methylsulfonyl-D-diphenylalanyl-L-prolyl-[(5-aminomethyl-3-thienyl)methyl]amide,
19. N-methoxycarbonyl-D-diphenylalanyl-L-prolyl-[(5-amidino-3-thienyl)methyl]amide,
20. N-cyclohexylsulfamoyl-D-diphenylalanyl-L-prolyl-[(5-amidino-2-thienyl)methyl]amide,
21. N-allyloxycarbonyl-D-diphenylalanyl-L-prolyl-[(5-amidino-2-thienyl)methyl]amide,
22. N-benzylsulfonyl-D-cyclohexylalanyl-L-prolyl-[(5-amidino-2-thienyl)methyl]amide,
23. N-cyclohexylsulfamoyl-D-cyclohexylalanyl-L-prolyl-[(5-amidino-2-thienyl)methyl]amide,
24. N-methylsulfamoyl-D-cylohexylalanyl-L-prolyl-[(5-amidino-2-thienyl)methyl]amide,
25. N-methylsulfonyl-D-cyclohexylglycinyl-L-prolyl-[(5-amidino-3-thienyl)methyl]amide,
26. N-(t-butoxycarbonyl)methyl-D-diphenylalanyl-L-prolyl-[(5-amidino-2-thienyl)methyl]amide,
27. N-(t-butoxycarbonyl)methyl-D-diphenylalanyl-L-prolyl-[(5-hydroxyamidino-2-thienyl)methyl]amide,
28. N-carboxymethyl-D-diphenylalanyl-L-prolyl-[(5-amidino-2-thienyl)methyl]amide,
29. N-methyl-N-carboxymethyl-D-diphenylalanyl-L-prolyl-[(5-amidino-2-thienyl)methyl]amide,
30. N-hydroxysulfonyl-D-diphenylalanyl-L-prolyl-[(5-amidino-2-thienyl)methyl]amide,
31. N-methylsulfonyl-D-diphenylalanyl-L-azetidine-2-carboxyl-[(5-amidino-2-thienyl)methyl]amide,
32. N-methylsulfonyl-D-diphenylalanyl-L-prolyl-[(4-amidino-5-methyl-2-thienyl)methyl]amide,
33. N-methylsulfonyl-D-diphenylalanyl-L-prolyl-[(5-amidino-2-furanyl)methyl]amide,
34. N-methoxycabonyl-D-diphenylalanyl-L-prolyl-[(5-amidino-2-furanyl)methyl]amide,
35. N-aminosulfonyl-D-diphenylalanyl-L-prolyl-[(5-amidino-3-furanyl)methyl]amide,
36. N-aminosulfonyl-D-diphenylalanyl-L-prolyl-[(4-amidino-2-thiazolyl)methyl]amide,
37. N-methylsulfonyl-D-diphenylalanyl-L-prolyl-[(5-amidino-1-methyl-2-pyrrolyl)methyl]amide,
38. N-carboxymethyl-D-diphenylalanyl-L-prolyl-[(5-amidino-3-thienyl)methyl]amide,
39. N-carboxymethyl-D-diphenylalanyl-L-prolyl-[(4-amidino-2-thiazolyl)methyl]amide,
40. N-[2-(methoxycarbonyl)ethyl]-D-diphenylalanyl-L-prolyl-[(5-amidino-2-thienyl)methyl]amide
41. N-(2-carboxyethyl)-D-diphenylalanyl-L-prolyl-[(5-amidino-2-thienyl)methyl]amide,
42. N-Boc-D-Diphenylalanyl-L-prolyl-[(5-amidrazono-2-thienyl)methyl]amide,
43. D-diphenylalanyl-L-prolyl-[(5-amidrazono-2-thienyl)methyl]amide,
44. N-methoxycabonyl-D-diphenylalanyl-L-azetidine-2-carboxyl-[(5-amidino-2-thienyl)methyl]amide,
45. N-(2-carboxyethyl)-D-diphenylalanyl-L-azetidine-2-carboxyl-[(5-amidino-2-thienyl)methyl]amide,
46. N-carboxymethyl-D-diphenylalanyl-L-prolyl-[(5-hydroxyamidino-2-thienyl)methyl]amide,
47. N-(methoxycarbonyl)methyl-D-diphenylalanyl-L-prolyl-[(5-hydroxyamidino-2-thienyl)methyl]amide,
48. D-diphenylalanyl-L-prolyl-[(5-amidino-2-thienyl)methyl]amide,
49. N-(3-carboxypropyl)-D-diphenylalanyl-L-prolyl-[(5-amidino-2-thienyl)methyl]amide,
50. N-(MeO)$_2$P(O)-D-diphenylalanyl-L-prolyl-[(5-amidino-2-thienyl)methyl]amide,
51. N-(Me)$_2$P(O)-D-diphenylalanyl-prolyl-[(5-amidino-2-thienyl)methyl]amide,
52. N-(HO)$_2$P(O)-D-diphenylalanyl-L-prolyl-[(5-amidino-2-thienyl)methyl]amide,
53. N-methyl-D-diphenylalanyl-L-prolyl-[(5-amidino-2-thienyl)methyl]amide,
54. N-phenyl-D-diphenylalanyl-L-prolyl-[(5-amidino-2-thienyl)methyl]amide,
55. N-[(N, N-diethylcarboxamido) methyl]-D-diphenylalanyl-L-prolyl-[(5-amidino-2-thienyl)methyl]amide, 56. N-[(N,N-diethylcarboxamido)ethyl]-D-diphenylalanyl-L-prolyl-[(5-amidino-2-thienyl)methyl]amide,
57. N-aminosulfonyl-D-diphenylalanyl-L-prolyl-[(5-amidino-2-thiazolyl)methyl]amide,
58. N-aminosulfonyl-D-diphenylalanyl-L-prolyl-[(2-amidino-4-thiazolyl)methyl]amide,
59. N-aminosulfonyl-D-diphenylalanyl-L-prolyl-[(4-amidino-2-thiazolyl)methyl]amide,
60. N-aminosulfonyl-D-diphenylalanyl-L-prolyl-[(2-amidino-5-thiazolyl)methyl]amide,
61. N-methylsulfonyl-D-diphenylalanyl-L-prolyl-[(5-amidino-2-thiazolyl)methyl]amide,
62. N-methylsulfonyl-D-diphenylalanyl-L-prolyl-[(2-amidino-4-thiazolyl)methyl]amide,
63. N-methylsulfonyl-D-diphenylalanyl-L-prolyl-[(4-amidino-2-thiazolyl)methyl]amide,
64. N-methylsulfonyl-D-diphenylalanyl-L-prolyl-[(2-amidino-5-thiazolyl)methyl]amide,
65. N-methoxycarbonyl-D-diphenylalanyl-L-prolyl-[(5-amidino-2-thiazolyl)methyl]amide,
66. N-methoxycarbonyl-D-diphenylalanyl-L-prolyl-[(2-amidino-4-thiazolyl)methyl]amide,
67. N-methoxycarbonyl-D-diphenylalanyl-L-prolyl-[(4-amidino-2-thiazolyl)methyl]amide,
68. N-methoxycarbonyl-D-diphenylalanyl-L-prolyl-[(2-amidino-5-thiazolyl)methyl]amide,
69. N-carboxymethyl-D-diphenylalanyl-L-prolyl-[(5-amidino-2-thiazolyl)methyl]amide,
70. N-carboxymethyl-D-diphenylalanyl-L-prolyl-[(2-amidino-4-thiazolyl)methyl]amide,
71. N-carboxymethyl-D-diphenylalanyl-L-prolyl-[(2-amidino-5-thiazolyl)methyl]amide,
72. N-aminosulfonyl-D-diphenylalanyl-L-prolyl-[(5-amidino-2-oxazolyl)methyl]amide,
73. N-aminosulfonyl-D-diphenylalanyl-L-prolyl-[(2-amidino-4-oxazolyl)methyl]amide,
74. N-aminosulfonyl-D-diphenylalanyl-L-prolyl-[(4-amidino-2-oxazolyl)methyl]amide,
75. N-aminosulfonyl-D-diphenylalanyl-L-prolyl-[(4-amidino-2-oxazolyl)methyl]amide,
76. N-methylsulfonyl-D-diphenylalanyl-L-prolyl-[(5-amidino-2-oxazolyl)methyl]amide,
77. N-methylsulfonyl-D-diphenylalanyl-L-prolyl-[(2-amidino-4-oxazolyl)methyl]amide,
78. N-methylsulfonyl-D-diphenylalanyl-L-prolyl-[(4-amidino-2-oxazolyl)methyl]amide,
79. N-methylsulfonyl-D-diphenylalanyl-L-prolyl-[(2-amidino-4-oxazolyl)methyl]amide,
80. N-methoxycarbonyl-D-diphenylalanyl-L-prolyl-[(5-amidino-2-oxazolyl)methyl]amide,
81. N-methoxycarbonyl-D-diphenylalanyl-L-prolyl-[(2-amidino-4-oxazolyl)methyl]amide,
82. N-methoxycarbonyl-D-diphenylalanyl-L-prolyl-[(4-amidino-2-oxazolyl)methyl]amide,
83. N-methoxycarbonyl-D-diphenylalanyl-L-prolyl-[(2-amidino-5-oxazolyl)methyl]amide,
84. N-carboxymethyl-D-diphenylalanyl-L-prolyl-[(5-amidino-2-oxazolyl)methyl]amide,
85. N-carboxymethyl-D-diphenylalanyl-L-prolyl-[(2-amidino-4-oxazolyl)methyl]amide,
86. N-carboxymethyl-D-diphenylalanyl-L-prolyl-[(4-amidino-2-oxazolyl)methyl]amide,
87. N-carboxymethyl-D-diphenylalanyl-L-prolyl-[(2-amidino-5-oxazolyl)methyl]amide,
88. N-aminosulfonyl-D-diphenylalanyl-L-prolyl-[(2-amidino-4-isoxazolyl)methyl]amide,
89. N-aminosulfonyl-D-diphenylalanyl-L-prolyl-[(4-amidino-2-isoxazolyl)methyl]amide,
90. N-methylsulfonyl-D-diphenylalanyl-L-prolyl-[(2-amidino-4-isoxazolyl)methyl]amide,
91. N-methylsulfonyl-D-diphenylalanyl-L-prolyl-[(4-amidino-2-isoxazolyl)methyl]amide,
92. N-methoxycarbonyl-D-diphenylalanyl-L-prolyl-[(2-amidino-4-isoxazolyl)methyl]amide,
93. N-methoxycarbonyl-D-diphenylalanyl-L-prolyl-[(4-amidino-2-isoxazolyl)methyl]amide,
94. N-carboxymethyl-D-diphenylalanyl-L-prolyl-[(4-amidino-2-isoxazolyl)methyl]amide,
95. N-carboxymethyl-D-diphenylalanyl-L-prolyl-[(2-amidino-4-isoxazolyl)methyl]amide,
96. N-aminosulfonyl-D-diphenylalanyl-L-prolyl-[(4-amidino-2-isoxazolyl)methyl]amide,
97. N-methylsulfonyl-D-diphenylalanyl-L-prolyl-[(4-amidino-2-pyrazolyl)methyl]amide,
98. N-methoxycarbonyl-D-diphenylalanyl-L-prolyl-[(4-amidino-2-pyrazolyl)methyl]amide,
99. N-carboxymethyl-D-diphenylalanyl-L-prolyl-[(4-amidino-2-pyrazolyl)methyl]amide,
100. N-aminosulfonyl-D-diphenylalanyl-L-prolyl-[(5-amidino-2-pyrrolyl)methyl]amide,
101. N-aminosulfonyl-D-diphenylalanyl-L-prolyl-[(4-amidino-2-pyrrolyl)methyl]amide,
102. N-aminosulfonyl-D-diphenylalanyl-L-prolyl-[(5-amidino-3-pyrrolyl)methyl]amide,
103. N-methylsulfonyl-D-diphenylalanyl-L-prolyl-[(5-amidino-2-pyrrolyl)methyl]amide,
104. N-methylsulfonyl-D-diphenylalanyl-L-prolyl-[(4-amidino-2-pyrrolyl)methyl]amide,
105. N-methylsulfonyl-D-diphenylalanyl-L-prolyl-[(5-amidino-3-pyrrolyl)methyl]amide,
106. N-methoxycarbonyl-D-diphenylalanyl-L-prolyl-[(5-amidino-2-pyrrolyl)methyl]amide,
107. N-methoxycarbonyl-D-diphenylalanyl-L-prolyl-[(4-amidino-2-pyrrolyl)methyl]amide,
108. N-methoxycarbonyl-D-diphenylalanyl-L-prolyl-[(5-amidino-3-pyrrolyl)methyl]amide,
109. N-carboxymethyl-D-diphenylalanyl-L-prolyl-[(5-amidino-2-pyrrolyl)methyl]amide,
110. N-carboxymethyl-D-diphenylalanyl-L-prolyl-[(4-amidino-2-pyrrolyl)methyl]amide,
111. N-carboxymethyl-D-diphenylalanyl-L-prolyl-[(5-amidino-3-pyrrolyl)methyl]amide,
112. N-aminosulfonyl-D-dicyclohexylalanyl-L-prolyl-[(5-amidino-2-thienyl)methyl]amide,
113. N-methylsulfonyl-D-diphenylalanyl-L-prolyl-[(5-amidino-2-pyrrolyl)methyl]amide,
114. N-carboxymethyl-D-dicyclohexylalanyl-L-prolyl-[(5-amidino-2-thienyl)methyl]amide,
115. N-aminosulfonyl-D-bis-(para-methoxyphenyl)alanyl-L-prolyl-[(5-amidino-2-thienyl)methyl]amide,
116. N-methoxycarbonyl-D-diphenylalanyl-L-prolyl-[(5-amidino-2-thienyl)methyl]amide,
117. N-methoxycarbonyl-D-bis-(para-methoxyphenyl)alanyl-L-prolyl-[(5-amidino-2-thienyl)methyl]amide,
118. N-carboxymethyl-D-bis-(para-methoxyphenyl)alanyl-L-prolyl-[(5-amidino-2-thienyl)methyl]amide,
119. N-aminosulfonyl-D-bis-(para-aminophenyl)alanyl-L-prolyl-[(5-amidino-2-thienyl)methyl]amide,
120. N-metylsulfonyl-D-bis-(para-aminophenyl)alanyl-L-prolyl-[(5-amidino-2-thienyl)methyl]amide,
121. N-methoxycarbonyl-D-bis-(para-aminophenyl)alanyl-L-prolyl-[(5-amidino-2-thienyl)methyl]amide,
122. N-carboxymethyl-D-bis-(para-aminophenyl)alanyl-L-prolyl-[(5-amidino-2-thienyl)methyl]amide,
123. N-aminosulfonyl-D-bis-(para-chlorophenyl)alanyl-L-prolyl-[(5-amidino-2-thienyl)methyl]amide, 124. N-methylsulfonyl-D-bis-(para-chlorophenyl)alanyl-L-prolyl-[(5-amidino-2-thienyl)methyl]amide,
125. N-methoxycarbonyl-D-bis-(para-chlorophenyl)alanyl-L-prolyl-[(5-amidino-2-thienyl)methyl]amide,
126. N-carboxymethyl-D-bis-(para-chlorophenyl)alanyl-L-prolyl-[(5-amidino-2-thienyl)methyl]amide.

Compounds of the present invention can be prepared according to the general procedure outlined below:

As exemplified by Example 1 and Example 8 (Scheme 1), a protected amino acid such as N-Boc-D-diphenylalnine is coupled to proline methyl ester using a couplng agent such as EDC and HOBT. The resultant dipeptide is treated with a strong acid such as hydrochloric acid gas or trifluoroacetic acid to remove the t-butoxycarbonyl (Boc) protecting group. The resultant free amine is reacted with a sulfonylating reagent such as sulfamoyl chloride and a base such as triethylamine. Carbamates-containing compounds are prepared using chloroformates. The product is then hydrolyzed with base such as lithium hydroxide, and the resultant acid is coupled to the desired amine such as 5-(aminomethyl)thiophene-2-carbonitrile. The coupled product is converted to the amidine by a three-step sequence involving sequential treatment with hydrogen sulfide, methyl iodide, and ammonium acetate. The amidrazone compound is obtained by treatment with hydrazine in place of ammonium acetate in the final step. The nitrile intermediate is also converted to the methylamine by catalytic hydrogenation in the presence of a strong acid such as hydrochloric acid.

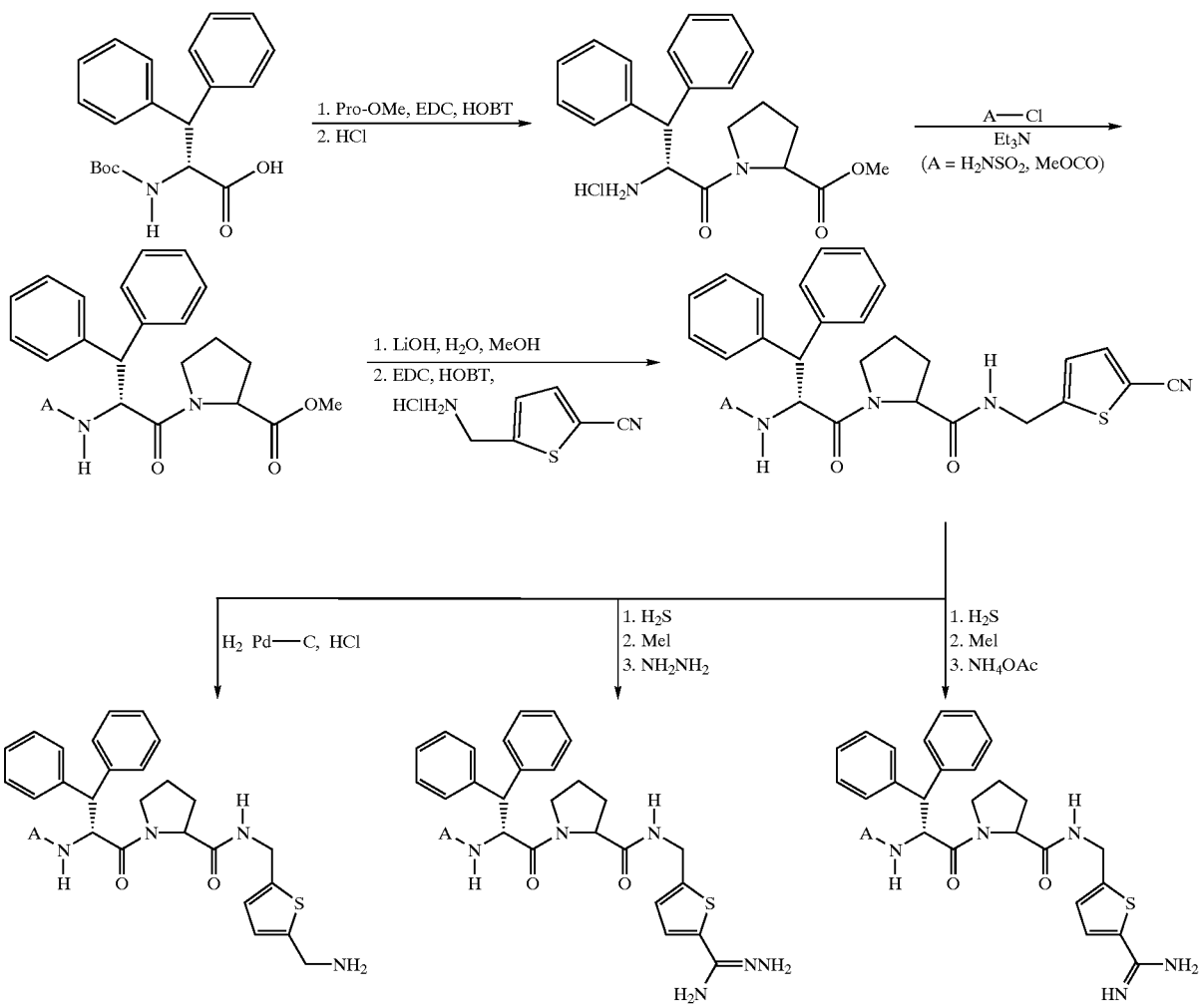

Scheme 1

An alternative route, as depicted in Scheme 2, is to hydrolyze the Boc-protected dipeptide before functionalizing the amino group and then couple the resultant acid with the desired amine. The protecting group of the coupling product is removed and the free amine is then sulfonylated.

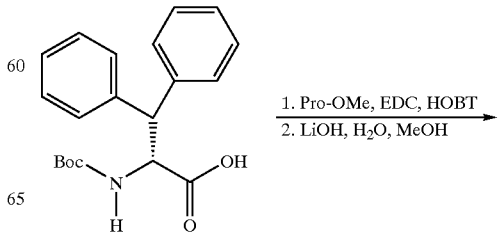

Scheme 2

-continued

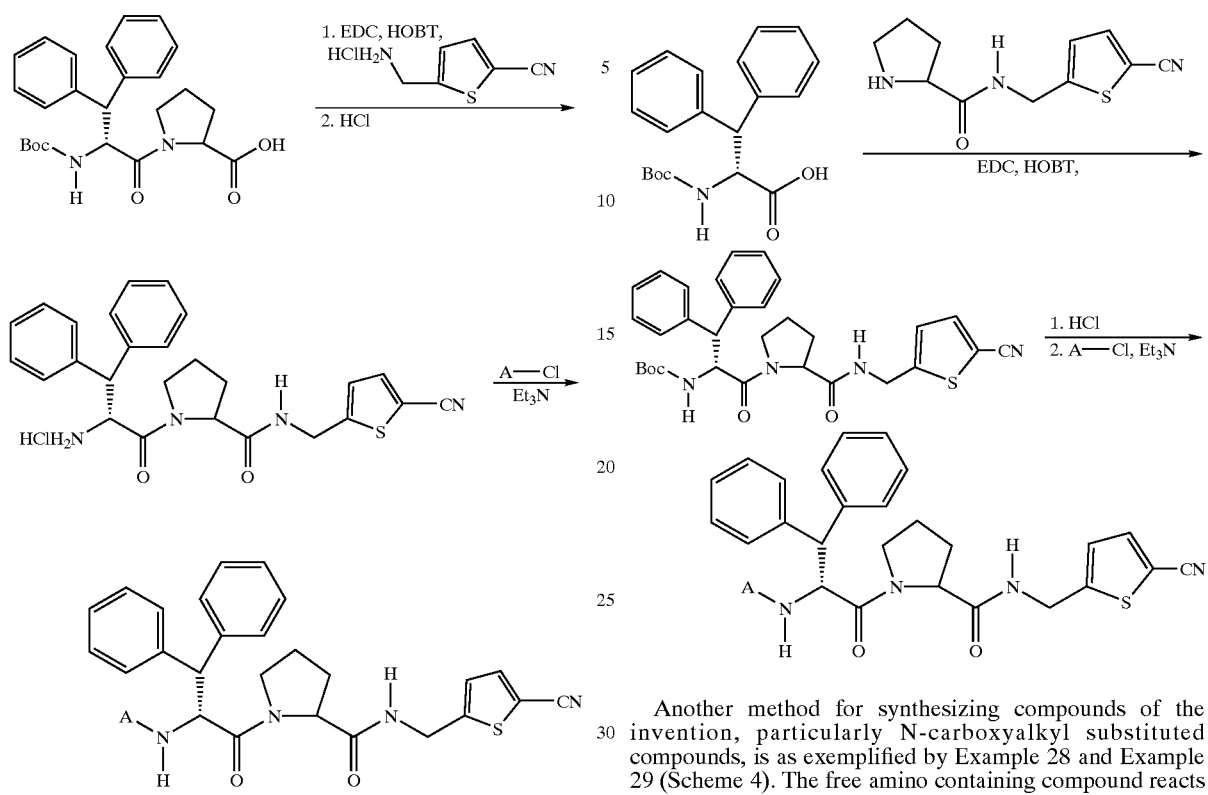

N-Boc-D-diphenylalnine can be coupled directly to the amine-coupled proline as exemplified by Example 32 (Scheme 3). The product is then deprotected and subsequently sulfonylated Another method for synthesizing compounds of the invention, particularly N-carboxyalkyl substituted compounds, is as exemplified by Example 28 and Example 29 (Scheme 4). The free amino containing compound reacts with an alkylating agent such as t-butylbromoacetate and a base such as diisopropylethylamine (DIPEA). The resulting compound is treated with hydroxylamine hydrochloride in the presence of base such as sodium carbonate, and the resultant amidoxime is catalytically hydrogenated in the presence of acetic anhydride to produce the amidine. The t-butyl group is removed with acid such as trifluoroacetic acid and hydrochloric acid to give the product.

Scheme 4

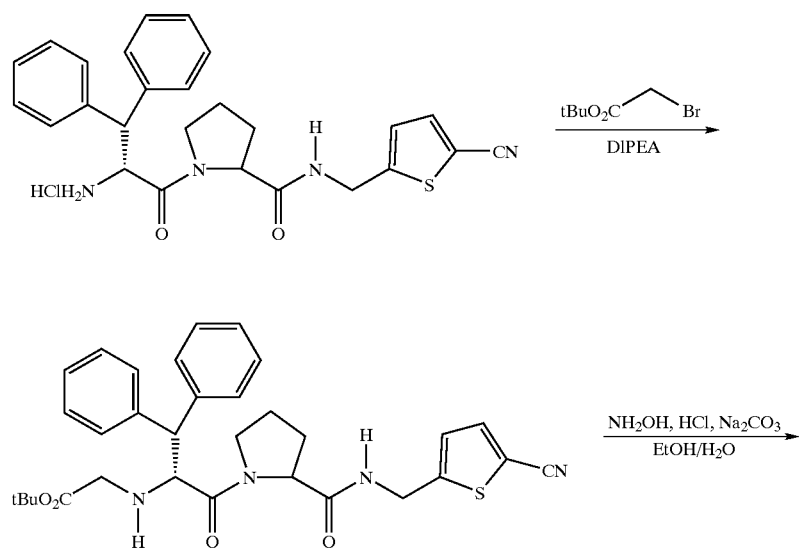

-continued

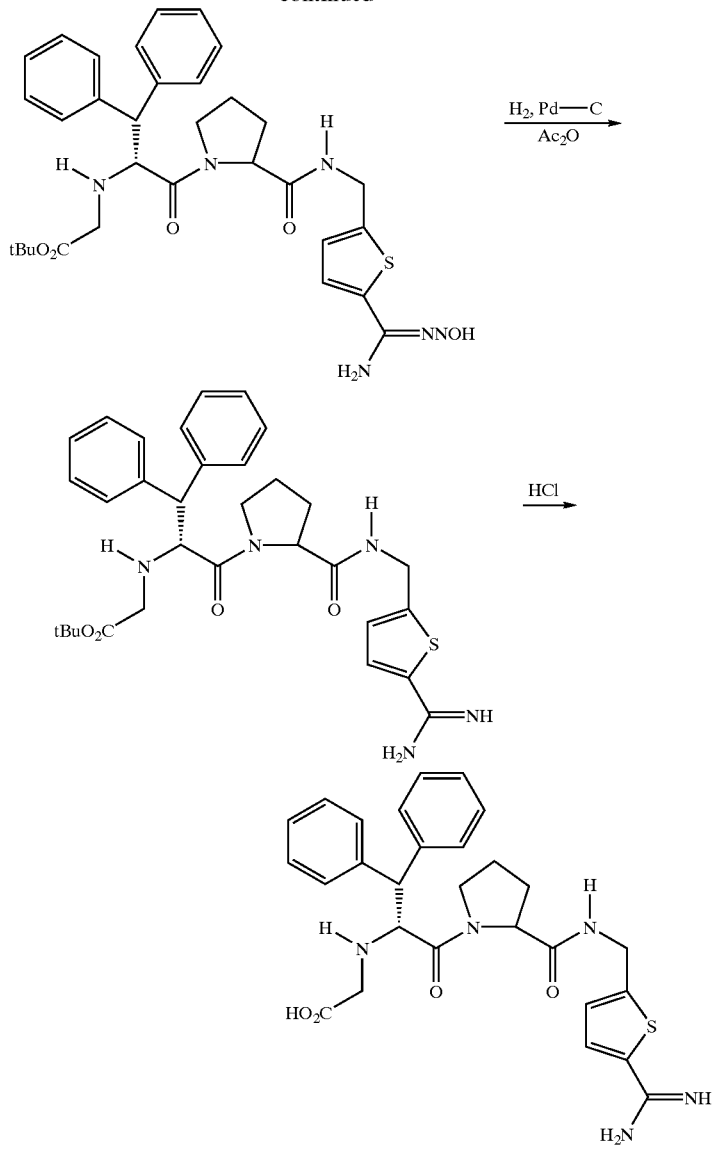

Amide coupling used to form the compounds of this invention are typically performed by the carbodiimide method with reagents such as dicyclohexylcarbodiimide (DCC) or 1-ethyl-3-(3-dimethylaminopropyl) carbodiimide (EDC). Other method for forming the amide or peptide bond include, but not limited to the synthetic routes via an acid chloride, azide, mixed anhydride or activated ester. The addition and removal of one or more protecting groups are typical practice. Methods for suitable protection and deprotection are provided in "Protective Groups in Organic Synthesis", 3rd Edition, by T. W. Green and Peter G. M. Wuts (1999), John Wiley & Sons, Inc., publishers.

The amide coupling reactions are carried out in an inert organic solvent such as dimethylformamide, dimethylacetamide, tetrahydrofuran, dichloromethane, chloroform, and like common solvents or a mixture of such solvents.

Compounds that potently regulate, modulate, or inhibit the conversion of fibrinogen to fibrin via the enzyme thrombin, and therefore inhibit thrombosis and clotting are desirable and represent preferred embodiments of the present invention. The present invention is further directed to methods of modulating trypsin-like serine protease activity, for example in mammalian tissue, by administering an inventive agent. The activity of the inventive compounds as modulators of trypsin-like serine protease activity, such as the activity of thrombin, may be measured by any of the methods available to those skilled in the art, including in vivo and/or in vitro assays. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the inventive agents are provided so as to provide therapeutic benefits involving modulation of tyrpsin-like serine proteases. By "efficacious levels" is meant levels in which the effects of tyrpsin-like serine proteases like thrombin are, at a minimum, regulated.

These compositions are prepared in unit-dosage form appropriate for the mode of administration, e.g., parenteral or oral administration.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, more preferably from about 0.001 to about 50 mg/kg body weight, and most preferably 1–20 mg/kg, with courses of treatment repeated at appropriate intervals. Administration of prodrugs are typically dosed at weight levels which are chemically equivalent to the weight levels of the fully active form. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form vial topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

Therapeutically effective amounts of the agents of the invention may be used to treat diseases mediated by modulation or regulation of trypsin-like serine proteases. An "effective amount" is intended to mean that amount of an agent that, when administered to a mammal in need of such treatment, is sufficient to effect treatment for a disease mediated by the activity of one or more trypsin-like serine proteases, such as thrombin. Thus, e.g., a therapeutically effective amount of a compound of the Formula I, salt, active metabolite or prodrug thereof is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more trypsin-like serine proteases, such as thrombin, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Proper formulation is dependent upon the route of administration chosen. The inventive compounds may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of table ts or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for us e in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be present e d in unit-dosage form, e.g., in ampoules or in multi-dose containers, with an added preservative. The compositions may take such forms as suspensions, solutions or emulsions in oily or aqueous vehicles, and may contain formulatory agents such as su spending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

The inventive agents may be prepared using the reaction routes and synthesis schemes as described below, employing the techniques available in the art using starting materials that are readily available.

The preparation of preferred compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully perfomed by modifications apparent to those skilled in the art, e.g. by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLE 1

Preparation of N-aminosulfonyl-D-diphenylalanyl-L-prolyl-[(5-amidino-2-thienyl)methyl]amide-TFA

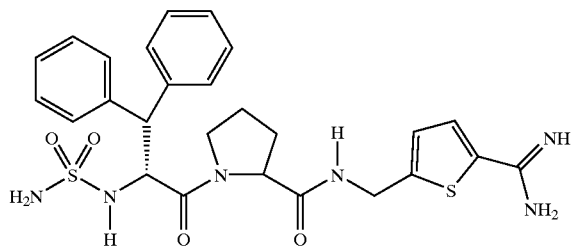

A) 5-(Bromomethyl)thiophene-2-carbonitrile

A mixture of 5-methylthiophene-2-carbonitrile (9.9 g, 80.5 mmol), benzoylperoxide (0.23 g, 0.95 mmol), and N-bromosuccinimide (15 g, 84.3 mmol) in carbontetrachloride (200 mL) was heated at reflux for 6 h. The resulting suspension was filtered and the filtrate diluted with dichloromethane (400 mL), washed with a saturated sodium bicarbonate solution, dried over magnesium sulfate, and concentrated in vacuo. The residue was purified by column chromatography (EtOAc: n-hexane, 1:4) to give the title compound as a yellow oil (14.0 g, 86%).

$^1$H NMR (CDCl$_3$) δ7.50 (d, 1H), 7.13 (d, 1 H), 4.68 (s, 2H). FAB MS: 203 [M+1]$^+$

B) 5-(Aminomethyl)thiophene-2-carbonitrile.HCl

To a cold solution of 5-(bromomethyl)thiophene-2-carbonitrile (4.2 g, 20.8 mmol) in THF (500 mL) was added sodium hydride (60% dispersion in oil, 1.0 g, 25 mmol) in portions. To this suspension was added di-t-butyl iminodicarboxylate (4.9 g, 22.9 mmol) in portions. After stirring for 3 h, the resulting solution was diluted with ethyl acetate (400 mL), washed with water, dried over magnesium sulfate, and concentrated in vacuo. The residue was purified by column chromatography (EtOAc: n-hexane, 1:4) to give 5-(N,N-Boc$_2$-aminomethyl)thiophene-2-carbonitrile as a yellow foam. This solid was dissolved in ethyl acetate (150 mL) and cooled to 0° C. HCl gas was bubbled through the solution for 10 min, and the mixture was allowed to warmed to room temperature. The solvent was removed in vacuo to give the title compound as a pale yellow solid (2.4 g, 86%).

$^1$H NMR (CD$_3$OD) δ7.48 (d, 1 H), 7.20 (d, 1H), 4.21 (s, 2H) FAB MS: 175 [M+1]$^+$

C) N-Aminosulfonyl-D-diphenylalanyl-L-proline methyl ester

To a stirring solution of chlorosulfonyl isocyanate (6.3 g, 45 mmol) in dichloromethane (25 mL) was added dropwise formic acid (2.13 g, 45 mmol). The mixture was heated at reflux for 5 h and cooled to obtain 1.8 N solution of sulfamoyl chloride in dichloromethane. To a cooled (0° C.) solution of D-diphenylalanyl-L-proline methyl ester.HCl (2.5 g, 6.47 mmol) in dichloromethane (100 mL) was added the 1.8 N sulfamoylchloride solution (6 mL) and triethylamine (2.7 mL). After the reaction was completed, the resulting solution was diluted with dichloromethane (40 mL), washed with brine, dried over magnesium sulfate, and concentrated in vacuo. The residue was purified by column chromatography (EtOAc: n-hexane, 2:1) to give the title compound (1.88 g, 67%).

$^1$H NMR (CDCl$_3$) δ7.38–7.20 (m, 4H), 7.18 (m, 6H), 5.85 (d, 1H), 5.29 (s, 2H), 4.95 (dd; 1H), 4.75 (m, 1H), 4.14 (d, 1H), 3.67 (s, 3H), 2.70 (m, 1H), 1.74 (m, 3H), 1.38 (m, 1 H). FAB MS: 431 [M+1]$^+$

D) N-Aminosulfonyl-D-diphenylalanyl-L-proline

To a suspension of N-aminosulfonyl-D-diphenylalanyl-L-proline methyl ester (1.88 g, 4.36 mmol) in a mixture of water (100 mL) and methanol (150 mL) was added 0.5 N lithium hydroxide (40 mL) and the mixture stirred overnight at rt. The resulting solution was acidified to pH 2 by addition of 1N HCl and the solvent partially removed by evaporation in vacuo. The precipitates were collected by filtration to give the title compound as a white crystalline solid (1.68 g, 92%).

$^1$H NMR (CD$_3$OD) δ7.40 (m, 2H), 7.33 (m, 2H), 7.24 (m, 6H), 4.95 (dd, 1H), 4.29 (d, 1H), 4.05 (m, 1H), 3.75 (m, 1H), 2.87 (m, 1H), 1.83–1.72 (m, 3H), 1.43 (m, 1H). FAB MS: 417 [M+1]$^+$

E) N-Aminosulfonyl-D-diphenylalanyl-L-prolyl-[(5-cyano-2-thienyl)methyl]amide

A mixture of N-aminosulfonyl-D-diphenylalanyl-L-proline (0.2 g, 0.48 mmol), 5-(aminomethyl)thiophene-2-carbonitrile.HCl (0.1 g, 0.57 mmol), EDC (0.14 g, 0.72 mmol), HOBT (0.08 g, 0.62 mmol), and triethylamine (0.2 mL, 1.44 mmol) in DMF (2 mL) was stirred for 2 h at rt. The solvent was removed in vacuo and the residue dissolved in EtOAc and washed sequentially with a saturated sodium bicarbonate solution, 1N HCl, and brine. After the solution was dried over magnesium sulfate and concentrated in vacuo, the residue was purified by column chromatography (EtOAc: n-hexane, 2:1) to give the title compound (0.2 g, 78%).

¹H NMR (CDCl₃) δ1.38 (m, 1H), 1.50 (m, 1H), 1.92 (m, 2H), 2.61 (m, 1H), 3.63 (m, 1H), 4.12 (m, 1H), 4.40 (m, 2H), 4.52 (m, 1H), 4.89 (m, 1H), 5.25 (m, 2H), 6.87 (m, 1H), 7.15–7.55 (m, 11H). FAB MS: 537 [M+1]⁺

F) N-Aminosulfonyl-D-diphenylalanyl-L-prolyl-[(5-amidino-2-thienyl)methyl]amide.TFA A solution of the coupling compound prepared in Step E (0.2 g, 0.37 mmol) in pyridine (2 mL) was saturated with gaseous H₂S. After the mixture was allowed to stand for 1 day, the solvent was removed in vacuo to obtain the thioamide as a yellow solid. To this material was added acetone (2 mL) and iodomethane (0.07 mL, 1.12 mmol), and the mixture was heated at reflux for 1 h. After the solvent was evaporated in vacuo, the resulting methylthioamidate was dissolved in acetonitrile (2 mL). To this solution was added ammonium acetate (0.09 g, 1.12 mmol) over 10 min and the mixture heated at reflux for 1 h. The solution was cooled and concentrated and the residue purified by column chromatography using 10% methanol in chloroform to give the title compound which was further purified by preparative HPLC (TFA (0.1%)-H₂O-MeOH gradient). The pure fractions were lyophilized to give a white solid (0.15 g, 60%) as a TFA salt.

¹H NMR (CD₃OD) δ1.46 (m, 1H), 1.62 (m, 1H), 1.73 (m, 1H), 1.85 (m, 1H), 2.90 (m, 1H), 3.76 (m, 1H), 4.05 (q, 1H), 4.31 (d, 1H), 4.59 (m, 1H), 4.62 (m, 1H), 4.98 (m, 1H), 7.25–7.51 (m, 11H), 7.77 (m, 1H). FAB MS: 555 [M+1]⁺

EXAMPLE 2

Preparation of N-aminosulfonyl-D-diphenylalanyl-L-prolyl-[(5-aminomethyl-2-thienyl)methyl]amide.HCl

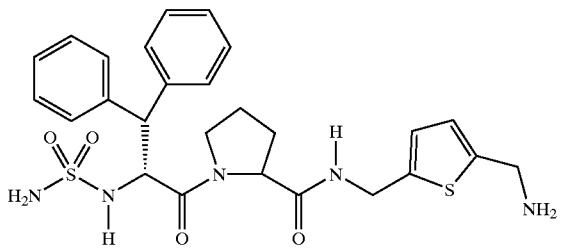

N-Aminosulfonyl-D-diphenylalanyl-L-prolyl-[(5-cyano-2-thienyl)methyl]amide prepared in Example 1, Step E (0.1 g, 0.19 mmol) was dissolved in methanol (2 mL). To this solution was added 10% palladium-on-carbon (100 mg) and 3 drops of conc. HCl and the mixture stirred for 2 days under H₂ (60 psi). The reaction mixture was filtered through Celite and the filtrate concentrated in vacuo. The residue was purified by preparative HPLC (TFA (0.1%)-H₂O-MeOH gradient) to give the title compound (40 mg, 36%) as a white solid.

¹H NMR (CD₃OD) δ1.41 (m, 1H), 1.50 (m, 1H), 1.72 (m, 1H), 1.82 (m, 1H), 2.98 (m, 1H), 3.75 (m, 1H), 4.05 (m, 3H), 4.38 (m, 3H), 4.98 (m, 1H), 7.20–7.51 (m, 12H). FAB MS: 542 [M+1]⁺

EXAMPLE 3

Preparation of N-methylsulfonyl-D-diphenylalanyl-L-prolyl-[(5-amidino-2-thienyl)methyl]amide.TFA

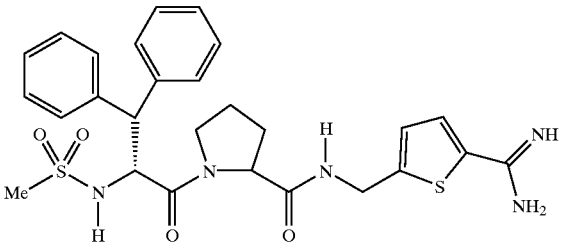

A) N-Methylsulfonyl-D-diphenylalanyl-L-proline

To a cooled (0° C.) solution of D-diphenylalanyl-L-proline methyl ester.HCl (2 g, 5.67 mmol) in dichloromethane (100 mL) was added methanesulfonylchloride (0.52 mL, 6.8 mmol) and triethylamine (3.1 mL, 22.7 mmol) and the mixture stirred for 2 h at rt. After the reaction was completed, the resulting mixture was washed with 1N HCl and then with brine, dried over magnesium sulfate, and concentrated in vacuo. The residue was purified by column chromatography (EtOAc: n-hexane, 1:2) to give N-methylsulfonyl-D-diphenylalanyl-L-proline methyl ester (2.1 g, 86%). This compound was then hydrolyzed essentially according to the procedure of Example 1, Step D to give the title compound (1.8 g, 90%).

¹H NMR (CD₃OD) δ1.45 (m, 1H), 1.70–1.90 (m, 3H), 2.91 (m, 4H), 3.85 (m, 1H), 4.11 (m, 1H), 4.32 (m, 1H), 4.98 (m, 1H), 7.18–7.42 (m, 10H). FAB MS: 417 [M+1]⁺

B) N-Methylsulfonyl-D-diphenylalanyl-L-prolyl-[(5-cyano-2-thienyl)methyl]amide

The title compound was prepared from N-methylsulfonyl-D-diphenylalanyl-L-proline and 5-(aminomethyl)thiophene-2-carbonitrile.HCl essentially according to the coupling procedure of Example 1, Step E; yield 88%. ¹H NMR (CDCl₃) δ1.45 (m, 2H), 1.72 (m, 1H), 2.06 (m, 1H), 2.56 (m, 1H), 2.80 (s, 3H), 3.61 (m, 1H), 4.28 (m, 1H), 4.36 (d, 1H), 4.50 (m, 2H), 4.83 (m, 1H), 5,44(m, 1H), 6.96 (m, 1H), 7.22–7.51 (m, 11H), FAB MS: 537 [M+1]⁺

C) N-Methylsulfonyl-D-diphenylalanyl-L-prolyl-[(5-amidino-2-thienyl)methyl]amide.TFA The title compound was prepared from the compound obtained in Step B using the procedure described in Example 1, Step F; yield 54%.

¹H NMR (CD₃OD) δ1.42 (m, 1H), 1.64 (m, 1H), 1.81 (m, 2H), 2.87 (s, 3H), 2.95 (m, 1H), 3.72 (m, 1H), 4.04 (m, 1H), 4.31 (d, 1H), 4.58 (m, 2H), 5.02 (m, 1H), 7.18–7.42 (m, 9H), 7.50 (m, 2H), 7.78 (m, 1H). FAB MS: 554 [M+1]⁺

EXAMPLE 4

Preparation of N-methylsulfonyl-D-diphenylalanyl-L-prolyl-[(5-amidrazono-2-thienyl)methyl]amide.TFA

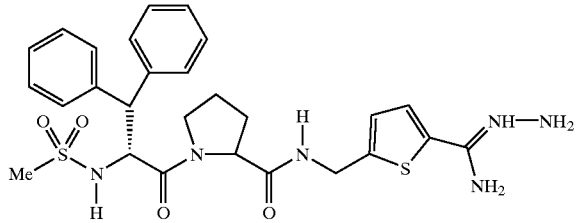

A solution of N-methylsulfonyl-D-diphenylalanyl-L-prolyl-[(5-cyano-2-thienyl)methyl]amide.TFA prepared in Example 3, Step B (0.2 g, 0.37 mmol) in pyridine (2 mL) was saturated with gaseous $H_2S$. After the mixture was allowed to stand for 1 days, the solvent was removed in vacuo. The yellow solid obtained was dissolved in acetone (2 mL) and iodomethane (0.07 mL, 1.12 mmol), and the mixture heated at reflux for 1h. After the solvent was evaporated in vacuo, the residue was dissolved in acetonitrile (2 mL). To this solution was added 80% hydrazine (0.07 mL, 1.12 mmol) over 10 min, and the mixture was stirred for 1h. The solution was concentrated and the crude product purified by preparative HPLC (TFA (0.1%)-$H_2O$-MeOH gradient) to give the title compound as a white solid (0.14 g, 55%).

$^1$H NMR ($CD_3OD$) δ1.39 (m, 1H), 1.52 (m, 1H), 1.80 (m, 2H), 2.92 (m, 4H), 3.69 (m, 1H), 4.03 (m, 1H), 4.31 (d,1H), 4.50 (m, 2H), 5.02 (m, 1H), 7.02 (m, 1H), 7.21–7.55 (m, 11 H). FAB MS: 569 [M+1]$^+$

EXAMPLE 5

Preparation of N-methylsulfonyl-D-diphenylalanyl-L-prolyl-[(5-aminomethyl-2-thienyl)methyl]amide.TFA

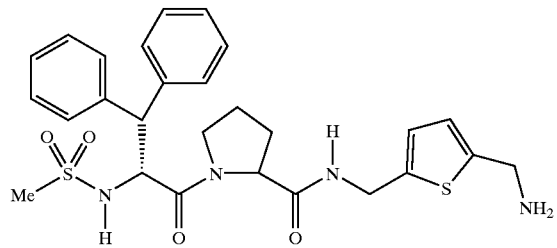

The title compound was prepared from N-methylsulfonyl-D-diphenylalanyl-L-prolyl-[(5-cyano-2-thienyl)methyl]amide.TFA (see Example 3, Step B) essentially using the procedure described in Example 2; yield 42%. $^1$H NMR ($CD_3OD$) δ1.47 (m, 1H), 1.60 (m, 1H), 1.79 (m, 2H), 2.84 (s, 3H), 2.93 (m, 1H), 3.71 (m, 1H), 4.03 (m, 1H), 4.31 (m, 3H), 4.46 (m, 2H), 4.98 (m, 1H), 7.25–7.50 (m, 12H). FAB MS: 541 [M+1]$^+$

EXAMPLE 6

Preparation of N-benzylsulfonyl-D-diphenylalanyl-L-prolyl-[(5-amidino-2-thienyl)methyl]amide.TFA

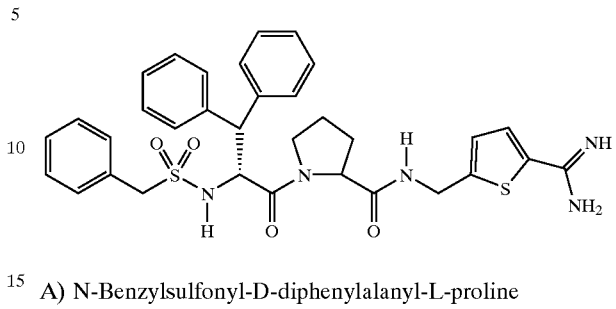

A) N-Benzylsulfonyl-D-diphenylalanyl-L-proline

This compound was prepared by the same procedure as described in Example 3, Step A except that benzylsulfonylchloride was used instead of methanesulfonylchloride; yield 46%.

$^1$H NMR ($CD_3OD$) δ1.40 (m, 1H), 1.68–1.88 (m, 3H), 2.88 (m, 1H), 3.93 (m, 1H), 4.15 (m, 1H), 4.37–4.43 (m, 3H), 5.02 (m, 1H), 7.17–7.48 (m, 15H). FAB MS: 493 [M+1]$^+$

B) N-Benzylsulfonyl-D-diphenylalanyl-L-prolyl-[(5-cyano-2-thienyl)methyl]amide

This compound was prepared from N-benzylsulfonyl-D-diphenylalanyl-L-proline using the procedure described in Example 1, Step E; yield 85%.

$^1$H NMR ($CDCl_3$) δ1.38 (m, 1H), 1.46 (m, 1H), 1.69 (m, 1H), 2.15 (m, 1H), 2.57 (m, 1H), 3.60 (m, 1H), 3.99 (d, 1H), 4.13 (d, 1H), 4.28 (m, 2H), 4.47 (m, 2H), 4.69 (m, 1H), 4.88 (m, 1H), 6.89 (m, 1H), 7.18 (m, 2H), 7.18–7.52 (m, 14H). FAB MS: 613 [M+1]$^+$

C) N-Benzylsulfonyl-D-diphenylalanyl-L-prolyl-[(5-amidino-2-thienyl)methyl]amide.TFA The title compound was prepared from the compound prepared in Step B using the procedure described in Example 1, Step F; yield 45%.

$^1$H NMR ($CD_3OD$) δ1.46 (m, 1 H), 1.62 (m, 1 H), 1.82 (m, 2H), 3.00 (m, 1 H), 3.78 (m, 1H), 4.03 (m, 1H), 4.21 (s, 2H), 4.32 (d, 1H), 4.59 (s, 2H), 5.12 (d, 1H), 7.09 (m 1H), 7.15–7.45 (m, 15H), 7.57 (m, 1H). FAB MS: 630 [M+1]$^+$

EXAMPLE 7

Preparation of N-t-butoxycarbonyl-D-diphenylalanyl-L-prolyl-[(5-amidino-2-thienyl)methyl]amide.TFA

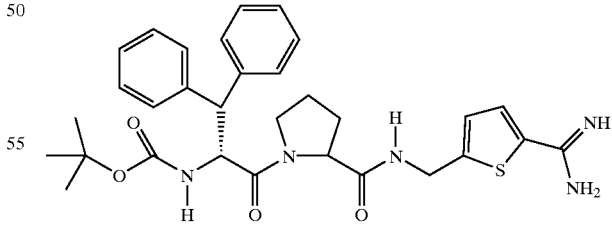

A) N-Boc-D-diphenylalanyl-L-prolyl-[(5-amidino-2-thienyl)methyl]amide

To a solution of N-Boc-D-diphenylalanyl-L-proline (2 g, 4.8 mmol) in DMF (20 mL) was added 5-(aminomethyl)thiophene-2-carbonitrile.HCl (1 g, 5.7 mmol, prepared in Example 1, Step B), EDC (1.4 g, 7.2 mmol), HOBT (0.8 g, 6.2 mmol), and triethylamine (2 mL, 14.4 mmol) and the mixture stirred overnight at rt. The solvent was removed in vacuo and the residue dissolved in EtOAc and washed sequentially with a saturated sodium bicarbonate solution, 1N HCl, and brine. After the solution was dried over magnesium sulfate and concentrated in vacuo, the residue was purified by column chromatography (EtOAc: n-hexane, 2:1) to give the title compound (2.3 g, 86%).

$^1$H NMR (CD$_3$OD) δ7.44 (m, 2H), 7.21 (m, 1H), 4.98 (s, 2H), 4.40 (m, 2H), 3.79 (m, 1H), 3.10–2.97 (m, 3H), 2.17–1.88 (m, 3H), 1.74 (m, 1H). FAB MS: 558 [M+1]$^+$

B) N-t-Butoxycarbonyl-D-diphenylalanyl-L-prolyl-[(5-amidino-2-thienyl)methyl]amide.TFA The title compound was prepared from the compound obtained in Step A using the procedure described in Example 1, Step F; yield 54%. $^1$H NMR (CD$_3$OD) δ7.78 (d, 1 H), 7.45 (m, 2H), 7.22 (m, 1 H), 7.16 (d, 1 H), (s, 2H), 4.59 (s, 2H), 4.40 (m, 2H), 3.81 (m, 1H), 3.09 (m, 1H), 2.96 (m, 2H), 1.98 FAB MS: 576 [M+1]$^+$

EXAMPLE 8

Preparation of N-methoxycarbonyl-D-diphenylalanyl-L-prolyl-[(5-amidino-2-thienyl)methyl]amide.TFA

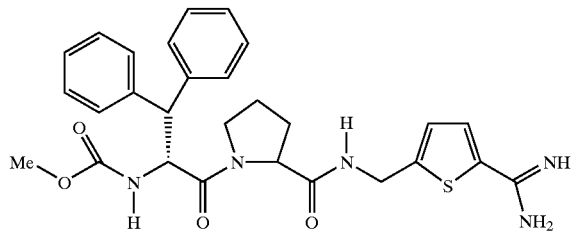

A) D-Diphenylalanyl-L-prolyl-[(5-cyano-2-thienyl)methyl]amide.HCl

To a cooled solution of N-Boc-D-diphenylalanyl-L-prolyl-[(5-cyano-2-thienyl)methyl]amide prepared in Example 7, Step A (0.2 g, 0.37 mmol) in methanol (20 mL) was added dropwise acetylchloride (2 mL). After stirring for 3 h at rt, the solution was removed to dryness to give the title compound as a white solid (0.271 g, 100%). $^1$H NMR (CDCl$_3$) δ8.52 (m, 1H), 7.55–7.12 (m, 11H), 6.84 (d, 1H), 4.77 (d, 1H), 4.57 (d, 1H), 4.50 (dd, 1H), 4.23 (d, 1H), 4.18 (dd, 1H), 3.77 (t, 1H), 2.43 (q, 1H), 194 (m, 1H), 1.62 (m, 1H), 1.48 (m, 1H), 1.30 (m, 1H) FAB MS: 459 [M+1]$^+$ B) N-Methoxycarbonyl-D-diphenylalanyl-L-prolyl-[(5-cyano-2-thienyl)methyl]amide D-Diphenylalanyl-L-prolyl-[(5-cyano-2-thienyl)methyl]amide.HCl (0.271 g) was dissolved in dichloromethane (2 mL) and cooled to 0° C. To this was added triethylamine (0.22 mL, 1.59 mmol) and methyl chloroformate (0.04 mL, 0.67 mmol) and the mixture stirred at rt for 2 h. The solution was concentrated and the residue purified by column chromatography (EtOAc: n-hexane, 2:1) to give the title compound (0.18 g, 67%).

$^1$H NMR (CDCl$_3$) δ1.50 (m, 1H), 1.67 (m, 1H), 1.88 (m, 2H), 3.01 (m, 1 H), 3.20 (s, 3H), 3.81 (m, 1H), 4.09 (m, 1H), 4.29 (d, 1H), 4.55 (m, 1H), 4.63 (m, 1H), 4.93 (m, 1H), 5.18 (m, 1H), 7.12–7.54 (m, 11 H), 7.68 (m, 1H). FAB MS: 516 [M+1]$^+$

C) N-Methoxycarbonyl-D-diphenylalanyl-L-prolyl-[(5-amidino-2-thienyl)methyl]amide The title compound was prepared from the compound obtained in Step B essentially according to the procedure of Example 1, Step F; yield 63%.

$^1$H NMR (CD$_3$OD) δ1.49 (m, 1H), 1.65 (m, 1H), 1.85 (m, 2H), 2.91 (m, 1H), 3.30 (s, 3H), 3.84 (m, 1H), 4.07 (m, 1H), 4.36 (m, 1H), 4.52 (m, 1H), 4.66 (m, 1H), 514 (m, 1H), 7.18–7.52 (m, 11H), 7.81 (m, 1H). FAB MS: 533 [M+1]$^+$

EXAMPLE 9

Preparation of N-aminosulfonyl-D-3,4-dichlorophenylalanyl-L-prolyl-[(5-amidino-2-thienyl)methyl]amide.TFA

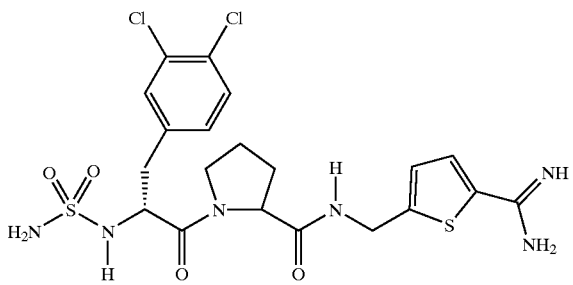

A) N-Aminosulfonyl-D-3,4-dichlorophenylalanyl-L-proline

The title compound was prepared from D-3,4-dichlorophenylalanyl-L-proline methyl ester (see J. Med. Chem. 1997, 40, 3726) using the procedure described in Example 1, Step C and D; yield 60%.

$^1$H NMR (CD$_3$OD) δ1.30 (m, 1H), 1.74 (m, 1H), 1.88–1.93 (m, 2H), 2.78 (m, 3H), 3.71 (m, 1H), 4.30–4.42 (m, 2H), 5.23 (m, 1H), 7.11–7.42 (m, 3H). FAB MS: 410 [M+1]$^+$

B) N-Aminosulfonyl-D-3,4-dichlorophenylalanyl-L-prolyl-[(5-amidino-2-thienyl)methyl]amide.TFA The title compound was prepared from the compound obtained Step A using the procedure described in Example 1, Step E and F; yield 32%.

$^1$H NMR (CD$_3$OD) δ1.38 (m, 1H), 1.67 (m, 1H), 1.84–2.01 (m, 2H), 2.84 (m, 2H), 3.02 (m, 1H), 3.88 (m, 1H), 4.25–4.52 (m, 4H), 7.18–7.62 (m, 5H). FAB MS: 547 [M+1]$^+$

EXAMPLE 10

Preparation of N-methoxycarbonyl-D-dicyclohexylalanyl-L-prolyl-[(5-amidino-2-thienyl)methyl]amide.TFA

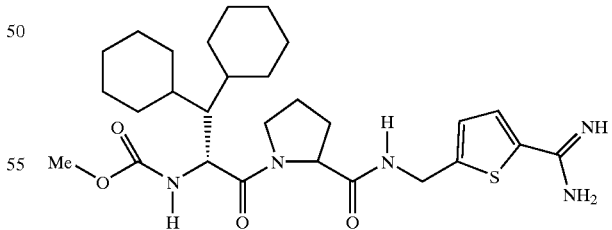

The title compound was prepared from D-dicyclohexylalanyl-L-proline methyl ester.HCl (see J. Med. Chem. 1997, 40, 3726) using the procedures described in Example 7, Step A and Example 8; yield 24%.

$^1$H NMR (CD$_3$OD) δ1.09–2.18 (m, 27H), 3.19–3.34 (m, 4H), 3.92 (m, 1H), 4.21–4.52 (m, 3H), 5.05 (m, 1H), 7.47 (m, 1 H), 7.71 (m, 1H) FAB MS: 546 [M+1]$^+$

EXAMPLE 11

Preparation of N-aminosulfonyl-D-diphenylalanyl-L-prolyl-[(4-amidino-2-thienyl)methyl]amide.TFA

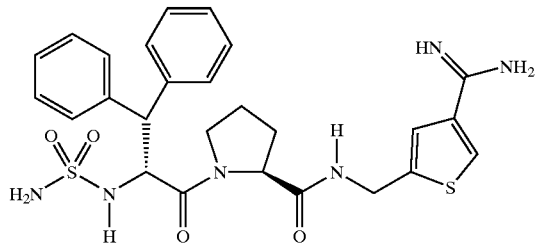

A) 4-Bromo-2-(hydroxymethyl)thiophene

4-Bromothiophene-2-carboxaldehyde (4 g, 18.8 mmol) was dissolved in dichloromethane/methanol (9/1, v/v, 100 mL) and the solution was cooled to 0° C. To this was added sodium borohydride (0.35 g, 9.4 mmol) and the mixture stirred for 3 h at rt. The reaction mixture was neutralized by addition of 1 N HCl, extracted with dichloromethane, and the extracts dried over magnesium sulfate and concentrated in vacuo. The residue was purified by column chromatography (EtOAc: n-hexane, 1:4) to give the title compound (3.5 g, 97%).

$^1$H NMR (CDCl$_3$) δ4.52 (s, 2H), 7.19 (m, 1H), 7.42 (m, 1H). FAB MS: 194 [M+1]$^+$

B) 2-(Hydroxymethyl)thiohene-4-carbonitrile

A mixture of 4-bromo-2-(hydroxymethyl)thiophene (3.5 g, 18.1 mmol) and cuprous cyanide (2.5 g, 28.2 mmol) in DMF (100 mL) was heated at reflux for 6 h. The reaction mixture was diluted with dichloromethane (100 mL), washed with aqueous ammonia, dried over magnesium sulfate, and concentrated in vacuo. The residue was purified by column chromatography (EtOAc: n-hexane, 2:1) to give the title compound (1.88 g, 75%).

$^1$H NMR (CDCl$_3$) δ4.46 (s, 2H), 7.12 (m, 1H), 7.46 (m, 1H) FAB MS: 140 [M+1]$^+$

C) 2-(Bromomethyl)thiophene-4-carbonitrile

To a cooled (0° C.) solution of 2-(hydroxymethyl)thiophene-4-carbonitrile (1.14 g, 8.2 mmol) in dichloromethane (50 mL) was added triphenylphosphine (2.8 g, 10.6 mmol) and carbon tetrabromide (3.3 g, 9.9 mmol). After stirring for 3 h at rt, the solvent was removed in vacuo and the residue chromatographed using EtOAc and n-hexane (1:4) to give the title compound (1.6 g, 96%).

$^1$H NMR (CDCl$_3$) δ4.38 (s, 2H), 7.15 (m, 1H), 7.40 (m, 1H) FAB MS: 203 [M+1]$^+$

D) 2-(Aminomethyl)thiophene-4-carbonitrile.HCl

This compound was prepared from 2-(bromomethyl)thiophene-4-carbonitrile (1.6 g, 8.0 mmol) using the procedure described in Example 1, Step B; yield 80%.

$^1$H NMR (CD$_3$OD) sm δ (m, 1H) FAB MS: 139 [M+1]$^+$

E) N-Aminosulfonyl-D-diphenylalanyl-L-prolyl-[(4-amidino-2-thienyl)methyl]amide.TFA This compound was prepared from 2-(aminomethyl)thiophene-4-carbonitrile.HCl and and N-aminosulfonyl-D-diphenylalanyl-L-proline using the procedure described in Example 1, Step E and F; yield 40%.

$^1$H NMR (CD$_3$OD) δ81.47 (m, 1H), 1.65 (m, 1H), 1.74 (m, 1H), 1.89 (m, 1H), 2.92 (m, 1H), 3.86 (m, 1H), 4.15 (m, 1H), 4.31 (m, 1H), 4.61 (m, 2H), 4.99 (m, 1H), 7.25–7.51 (m, 11H), 7.77 (m, 1 H) FAB MS: 555 [M+1]$^+$

EXAMPLE 12

Preparation of N-methylsulfonyl-D-diphenylalanyl-L-prolyl-[(4-amidino-2-thienyl)methyl]amide.TFA

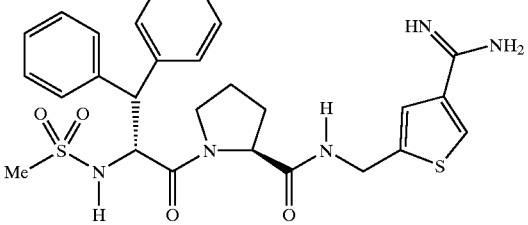

This compound was prepared from N-methylsulfonyl-D-diphenylalanyl-L-proline (Example 3, Step A) and 2-(aminomethyl)thiophene-4-carbonitrile.HCl (Example 11, Step D) essentially according to the procedure of Example 1, Step E and F; yield 59%.

$^1$H NMR (CDCl$_3$) δ1.51 (m, 1H), 1.64 (m, 1H), 1.92 (m, 2H), 2.91–3.01 (m, 4H), 3.72 (m, 1H), 4.12 (m, 1H), 4.28 (d, 1H), 4.55 (m, 2H), 5.07 (m, 1H), 7.18–7.52 (m, 11H), 7.74 (m, 1H) FAB MS: 554 [M+1]$^+$

EXAMPLE 13

Preparation of N-methylsulfonyl-D-diphenylalanyl-L-prolyl-[(4-aminomethyl-2-thienyl)methyl]amide.HCl

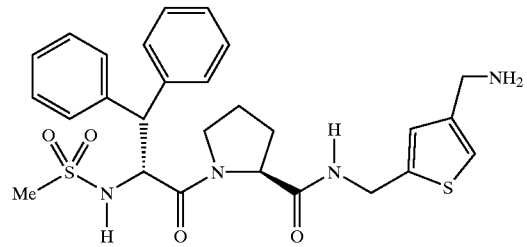

This compound was prepared from N-methylsulfonyl-D-diphenylalanyl-L-prolyl-[(4-cyano-2-thienyl)methyl]amide (Example 12) according to the procedure of Example 2; yield 38%.

$^1$H NMR (CD$_3$OD) δ1.42 (m, 1H), 1.65 (m, 1H), 1.81 (m, 2H), 2.78 (s, 3H), 2.90 (m, 1H), 3.82 (m, 1H), 4.11 (m, 1H), 4.35 (m, 3 H), 4.45 (m, 2H), 5.02 (m, 1H), 7.20–7.55 (m, 12H) FAB MS: 541 [M+1]$^+$

EXAMPLE 14

Preparation of N-methoxycarbonyl-D-diphenylalanyl-L-prolyl-[(4-amidino-2-thienyl)methyl]amide.TFA

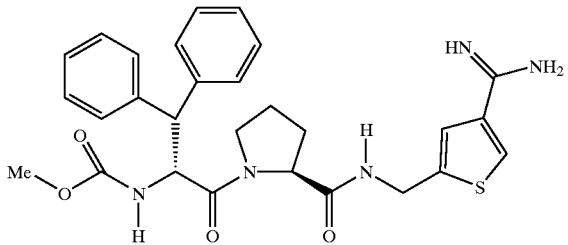

This compound was prepared from N-Boc-D-diphenylalanyl-L-proline and 2-(aminomethyl)thiophene-4-carbonitrile.HCl (Example 11, Step D) using the procedure described in Example 1, Step E and F; yield 32%.

$^1$H NMR (CD$_3$OD) δ1.49 (m, 1H), 1.65 (m, 1H), 1.82 (m, 2H), 2.92 (m, 1H), 3.45 (s, 3H), 3.83 (m, 1H), 4.07 (m, 1H), 4.36 (m, 2H), 4.59 (m, 1H), 5.14 (m, 1H), 7.18–7.48 (m, 11 H), 7.75 (m, 1H) FAB MS: 516 [M+1]$^+$

EXAMPLE 15

Preparation of N-aminosulfonyl-D-diphenylalanyl-L-prolyl-[(5-amidino-3-thienyl)methyl]amide.TFA

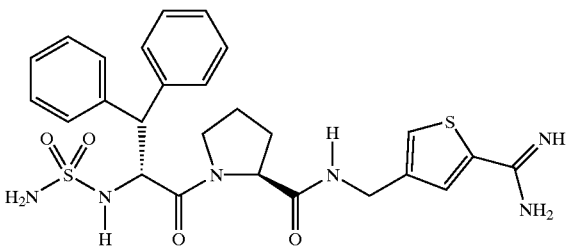

A) 2-Iodothiophene-4-carboxaldehyde

To a solution of 3-thiophenecarboxaldehyde (500 mg, 4.46 mmol) in a 1:1 mixture of acetic acid and water (10 mL) was added 95% sulfuric acid (0.31 mL). To this was added sequentially HIO$_4$ (305 mg, 1.34 mmol) and iodine (680 mg, 2.67 mmol) and the mixture stirred for 3 h at 60° C. After the reaction was completed, aqueous NaHSO$_3$ solution (6 mL) was added, the mixture basified to pH 12 by addition of 1 ON NaOH, and extracted with dichloromethane. The extracts were dried over magnesium sulfate and concentrated in vacuo. The residue was purified by column chromatography (EtOAc: n-hexane, 3:97) to give the title compound (390 mg, 37%).

$^1$H NMR (CDCl$_3$) δ9.76 (s, 1H), 8.08 (d, 1H), 7.68 (d, 1 H).

FAB MS: 239 [M+1]$^+$

B) 4-(Hydroxymethyl)-2-iodothiophene

A solution of 2-iodothiophene-4-carboxaldehyde (5 g, 21 mmol) in methanol (100 mL) was cooled to 0° C. To this was added sodium borohydride (1.2 g, 31.5 mmol) and the mixture was stirred for 30 min at 0° C. The reaction mixture was quenched by addition of saturated ammonium chloride solution and concentrated. The residue was dissolved in EtOAc, washed with brine, dried over magnesium sulfate, and concentrated in vacuo. The crude material was purified by column chromatography (EtOAc: n-hexane, 1:4); yield 4.53 g (90%).

$^1$H NMR (CDCl$_3$) δ7.15 (s, 2H), 4.52 (s, 2H). FAB MS: 241 [M+1]$^+$

C) 4-(Hydroxymethyl)thiohene-2-carbonitrile

This compound was prepared from 4-(hydroxymethyl)-2-iodothiophene (1.2 g, 5 mmol) using the procedure described in Example 11, Step A; yield 536 mg (77%).

$^1$H NMR (CDCl$_3$) δ7.58 (s, 1H), 7.48 (s, 1H), 4.47 (s, 2H). FAB MS: 140 [M+1]$^+$

D) 4-(Bromomethyl)thiophene-2-carbonitrile

This compound was prepared from 4-(hydroxymethyl)thiohene-2-carbonitrile (536 mg, 3.85 mmol) using the procedure described in Example 11, Step C; yield 754 mg (97%).

$^1$H NMR (CDCl$_3$) δ7.59 (s, 1H), 7.49 (s, 1H), 4.89 (s, 2H). FAB MS: 203 [M+1]$^+$

E) 4-(Aminomethyl)thiophene-2-carbonitrile.HCl

This compound was prepared from 4-(bromomethyl)thiophene-2-carbonitrile (188 mg, 4.7 mmol) using the procedure described in Example 1, Step B; yield 231 mg (95%).

$^1$H NMR (CD$_3$OD) δ7.75 (s, 1H), 7.64 (s, 1H), 4.65 (s, 2H). FAB MS: 139 [M+1]$^+$

F) N-Aminosulfonyl-D-diphenylalanyl-L-prolyl-[(5-amidino-3-thienyl)methyl]amide.TFA This compound was prepared from 4-(aminomethyl)thiophene-2-carbonitrile.HCl and N-aminosulfonyl-D-diphenylalanyl-L-proline using the procedure described in Example 1, Step E and F; yield 41%.

$^1$H NMR (CD$_3$OD) δ7.83(d, 1H), 7.82(d, 1H), 7.43 (m, 2H), 7.36 (m, 2H), 7.24 (m, 6H), 4.45(dd, 1H), 4.32 (d, 1H), 4.21 (dd, 1H), 4.04 (m, 1H), 3.76 (m, 1H), 2.88 (m, 1H), 1.83–1.45 (m, 4H). FAB MS: 555 [M+1]$^+$

EXAMPLE 16

Preparation of N-methylsulfonyl-D-diphenylalanyl-L-prolyl-[(5-amidino-3-thienyl)methyl]amide.TFA

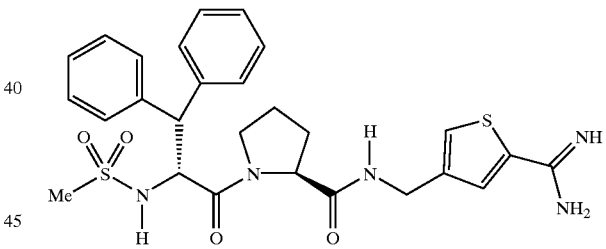

A) N-Methylsulfonyl-D-diphenylalanyl-L-prolyl-[(5-cyano-3-thienyl)methyl]amide

This compound was prepared from N-methylsulfonyl-D-diphenylalanyl-L-proline (Example 3, Step A) and 4-(aminomethyl)thiophene-2-carbonitrile.HCl (Example 15, Step E) using the procedure described in Example 1, Step E; yield 89%.

$^1$H NMR (CDCl$_1$) δ7.60 (d, 1 H), 7.38 (m, 5H), 7.23(m, 6H), 4.81 (dd, 1H), 4.39–4.36 (m, 3H), 4.23 (m, 1H), 3.58 (m, 1H), 2.83 (s, 3H), 2.55 (m, 1H), 1.41 (m, 2H). FAB MS: 537 [M+1]$^+$

B) N-Methylsulfonyl-D-diphenylalanyl-L-prolyl-[(5-amidino-3-thienyl)methyl]amide.TFA This compound was prepared from the compound obtained in Step A using the procedure described in Example 1, Step F; yield 53%.

$^1$H NMR (CD$_3$OD) δ7.62(d, 1H), 7.51(d, 1H), 7.54–7.23 (m, 10H), 4.99 (d, 1), 4.39(m, 4H), 4.11 (dd, 1H), 3.78 (m, 1H), 2.95(m, 1H), 2.90(s, 3H), 1.82–1.43 (m, 4H). FAB MS: 554[M+1]$^+$

EXAMPLE 17

Preparation of N-methylsulfonyl-D-diphenylalanyl-L-prolyl-[(5-amidrazono-3-thienyl)methyl]amide.TFA

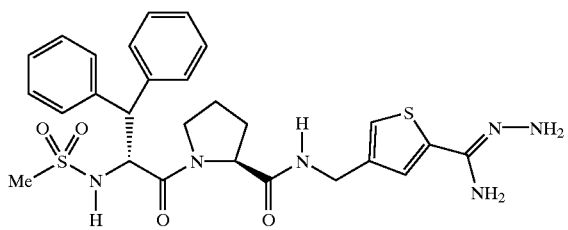

This compound was prepared from N-methylsulfonyl-D-diphenylalanyl-L-prolyl-[(5-cyano-3-thienyl)methyl]amide (Example 16, Step A) using the procedure described in Example 4; yield 63%.

$^1$H NMR (CD$_3$OD)δ7.52(d, 1H), 7.42 (d, 1H), 7.34–7.10 (m, 10H), 4.99 (d, 1H), 4.29(m, 3H), 4.00 (dd, 1H), 3.68 (m, 1H), 3.27 (m, 1H), 2.91 (m, 1H), 2.80(s, 3H), 1.79–1.32 (m, 4H). FAB MS: 569 [M+1]$^+$

EXAMPLE 18

Preparation of N-methylsulfonyl-D-diphenylalanyl-L-prolyl-[(5-aminomethyl-3-thienyl)methyl]amide.TFA

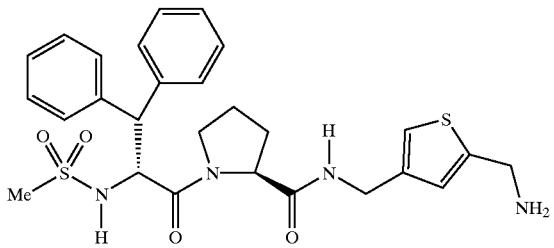

This compound was prepared from N-methylsulfonyl-D-diphenylalanyl-L-prolyl-[(5-cyano-3-thienyl)methyl]amide (Example 16, Step A) using the procedure described in Example 2; yield 75%.

$^1$H NMR (CD$_3$OD) δ7.47 (d, 2H), 7.36 (m, 2H), 7.26 (m, 6H), 6.93 (d, 1H), 6.87 (d, 1H), 5.00 (d, 1H), 4.44 (s, 2H), 4.30 (m, 2H), 4.12(s, 2H), 3.79 (m, 1H), 2.92 (m, 1H), 2.85 (s, 3H), 1.78–1.32 (m, 4H). FAB MS: 541 [M+1]$^+$

EXAMPLE 19

Preparation of N-methoxycarbonyl-D-diphenylalanyl-L-prolyl-[(5-amidino-3-thienyl)methyl]amide .TFA

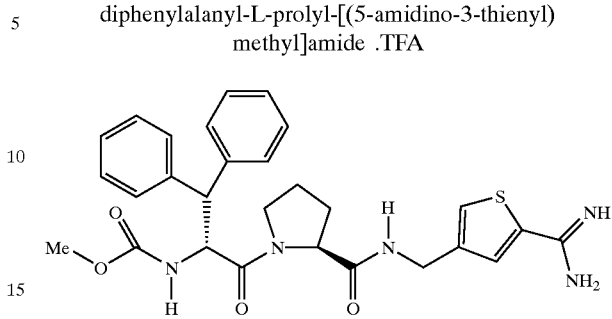

This compound was prepared from N-Boc-D-diphenylalanyl-L-proline and 4-(aminomethyl)thiophene-2-carbonitrile.HCl (Example 15, Step E) using the procedure described in Example 7, Step A, followed by Example 8; yield 47%.

$^1$H NMR (CD3OD) δ1.48 (m, 1H), 1.61 (m, 1H), 1.83 (m, 2H), 2.92 (m, 1 H), 3.45 (s, 3H), 3.81 (m, 1H), 4.08 (m, 1H), 4.37 (d, 1H), 4.55 (q, 2H), 5.15 (m, 1H), 7.15–7.49 (m, 12H). 7.49 (m, 12H). FAB MS: 516 [M+1]$^+$

EXAMPLE 20

Preparation of N-cyclohexylsulfamoyl-D-diphenylalanyl-L-prolyl-[(5-amidino-2-thienyl)methyl]amide.TFA

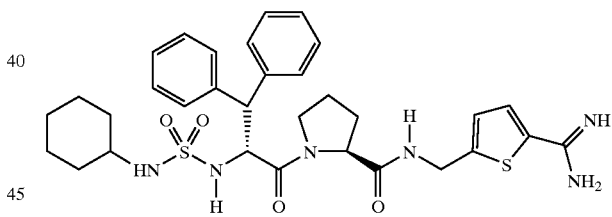

A) Cyclohexylsulfamoylchloride

To a solution of cyclohexylsulfamic acid (5 g, 27.9 mmol) in benzene (30 mL) was added dropwise phosphorus pentachloride (6.4 g, 30.7 mmol), and the mixture heated at reflux for 4 h. After the solvent was removed, the residue was distilled under reduced pressure to give the title compound (5 g, 91%).

B) N-cyclohexylsulfamoyl-D-diphenylalanyl-L-prolyl-[(5-amidino-2-thienyl)methyl]amide.TFA This compound was prepared from cyclohexylsulfamoylchloride essentially according to the procedure of Example 3; yield 41%.

$^1$H NMR (CD$_3$OD) δ7.76 (d, 1H), 7.49–7.10 (m, 10H), 7.03 (d, 1H), 4.97 (m, 1H), 4.60 (dd, 1H), 4.50 (dd, 1H), 4.30 (d, 1H), 4.04 (m, 1H), 3.85 (m, 1H), 3.05 (m, 1H), 2.73 (m, 1H), 1.86 (m, 3H), 1.75 (m, 2H), 1.55 (m, 3H), 1.28–1.00 (m, 6H). FAB MS: 637 [M+1]$^+$

EXAMPLE 21

Preparation of N-allyloxycarbonyl-D-diphenylalanyl-L-prolyl-[(5-amidino-2-thienyl)methyl]amide.TFA

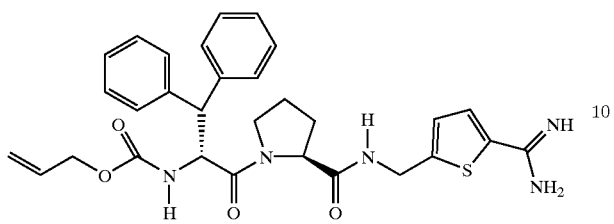

This compound was prepared from allylchloroformate essentially according to the procedure of Example 8; yield 56%.

$^1$H NMR (CD$_3$OD) δ7.79 (d, 1H), 7.41–7.18 (m, 10H), 7.12(d, 1H), 5.74 (m, 1H), 5.15 (d, 2H), 5.08 (d, 1H), 4.86(dd, 1H), 4.65(m, 1H), 4.53 (dd, 1H), 4.36 (d, 2H), 4.23 (dd, 1H), 4.09 (dd, 1H), 3.81 (m, 1H), 2.92 (m, 1H), 1.85–1.49 (m, 4H). FAB MS: 560 [M+1]$^+$

EXAMPLE 22

Preparation of N-methylsulfonyl-D-cyclohexylalanyl-L-prolyl-[(5-amidino-2-thienyl)methyl]amide.TFA

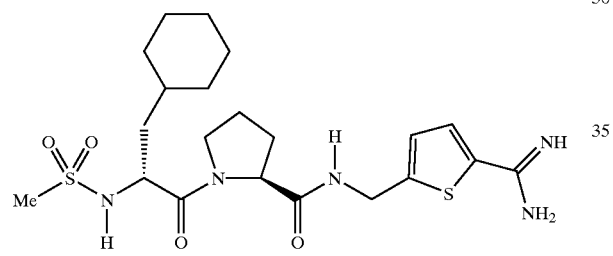

This compound was prepared from D-cyclohexylalanyl-L-proline methyl ester.HCl essentially according to the procedure of Example 3; yield 41%.

$^1$H NMR (CD$_3$OD) δ7.77 (d, 1H), 7.18 (d, 1H), 5.05(m, 1H), 4.58 (m, 2H), 4.41 (dd, 1H), 4.30 (dd, 1H), 3.85 (m, 1H), 3.39 (m, 1H), 2.85 (s, 3H), 2.23 (m, 1H), 2.12–1.15 (m, 15H), 1.10 (m, 2H) FAB MS: 484 [M+1]$^+$

EXAMPLE 23

Preparation of N-benzylsulfonyl-D-cyclohexylalanyl-L-prolyl-[(5-amidino-2-thienyl)methyl]amide.TFA

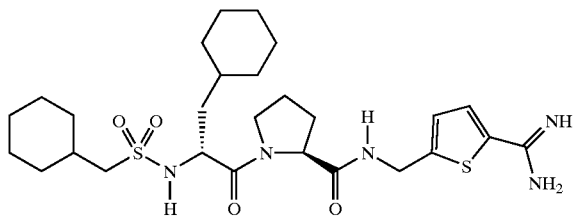

This compound was prepared from D-cyclohexylalanyl-L-proline methyl ester.HCl and benzylsulfonylchloride using the procedure described in Example 3; yield 45%.

$^1$H NMR (CD$_3$OD) δ7.68 (d, 1H), 7.52–7.30 (m, 5H), 7.12 (d, 1H), 4.98 (m, 1H), 4.56 (s, 2H), 4.42 (d, 1H), 4.32 (d, 1H), 4.22 (d, 1H), 4.12 (m, 1H), 3.77 (m, 1H), 3.46 (m, 1H), 2.21 (m, 1H), 2.04 (m, 3H), 1.92–1.12 (m, 11H), 0.95 (m, 2H). FAB MS: 560 [M+1]$^+$

EXAMPLE 24

Preparation of N-cyclohexylsulfamoyl-D-cyclohexylalanyl-L-prolyl-[(5-amidino-2-thienyl)methyl]amide.TFA

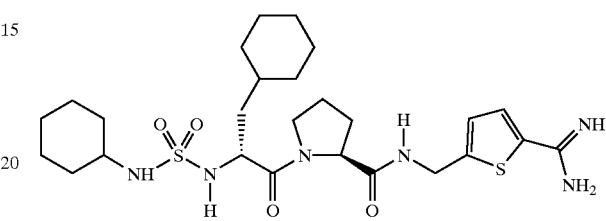

This compound was prepared from D-cyclohexylalanyl-L-proline.HCl and cyclohexylsulfamoylchloride using the procedure described in Example 3; yield 39%.

$^1$H NMR (CD$_3$OD) δ7.43 (d, 1 H), 6.95 (d, 1H), 4.62 (m, 3H), 4.45 (dd, 1 H), 4.27 (m, 1H), 4.12 (m, 1H), 3.42 (m, 1H), 3.22 (m, 1H), 2.37 (m, 1H), 2.20–1.10 (m, 24H), 0.91 (m, 2H) FAB MS: 567 [M+1]$^+$

EXAMPLE 25

Preparation of N-methylsulfamoyl-D-cyclohexylalanyl-L-prolyl-[(5-amidino-2-thienyl)methyl]amide.TFA

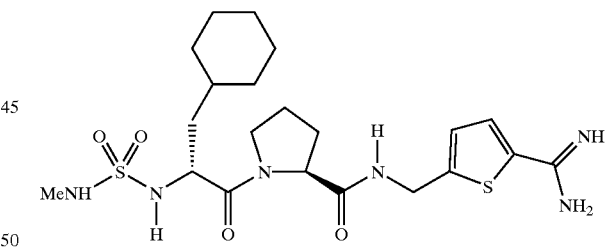

A) Methylsulfamoylchloride

This compound was prepared from methylsufamic acid (5 g, 45.9 mmol) using the procedure described in Example 20, Step A; yield 70%.

B) N-Methylsulfamoyl-D-cyclohexylalanyl-L-prolyl-[(5-amidino-2-thienyl)methyl]amide.TFA This compound was prepared from D-cyclohexylalanyl-L-proline.HCl and methylsulfamoylchloride using the procedure described in Example 3; yield 30%.

$^1$H NMR (CD$_3$OD) δ7.84 (d, 1H), 7.20 (d, 1H), 4.59 (m, 2H), 4.42 (m, 1H), 4.18 (m, 1H), 3.92 (m, 1H), 3.55 (m, 1H), 2.53 (s, 3H), 2.22 (m, 1H), 2.02 (m, 3H) 1.91–1.15 (m, 11H), 1.01 (m, 2H) FAB MS: 499 [M+1]$^+$

EXAMPLE 26

Preparation of N-methylsulfonyl-D-cyclohexylglycinyl-L-prolyl-[(5-amidino-3-thienyl)methyl]amide.TFA

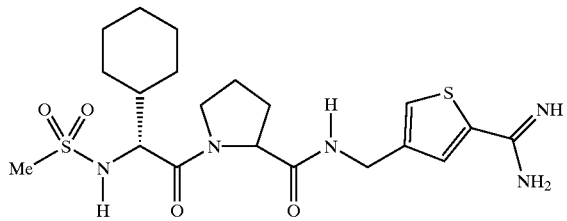

This compound was prepared from D-cyclohexylglycinyl-L-proline methyl ester.HCl and 4-(aminomethyl)thiophene-2-carbonitrile.HCl (Example 15, Step F) essentially according to the procedure of Example 3; yield 46%.

$^1$H NMR (CD$_3$OD) δ7.85(s, 1H), 7.84 (s, 1H), 4.45(dd, 1H), 4.37(d, 2H), 4.01 (d, 1H), 3.89 (m, 1H), 3.68 (m, 1H), 2.90 (s, 3H), 2.24–1.05 (m, 14H). FAB MS: 470 [M+1]$^+$

EXAMPLE 27

Preparation of N-methoxycarbonyl-D-cyclohexylglycinyl-L-prolyl-[(5-amidino-3-thienyl)methyl]amide.TFA

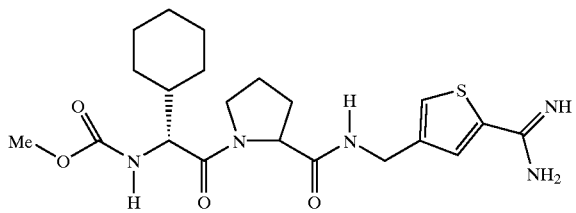

This compound was prepared from N-Boc-D-cyclohexylglycinyl-L-proline and 4-(aminomethyl)thiophene-2-carbonitrile.HCl (Example 15, Step F) essentially according to the procedures of Example 7, Step A and Example 8; yield 42%.

$^1$H NMR (CD$_3$OD) δ7.82(s, 1H), 7.75 (s, 1H), 4.55 (d, 2H), 4.48(d, 1H), 4.33(d, 1H), 4.14 (d, 1H), 4.02 (m, 1H), 3.69 (m, 1 H); 3.39 (s, 3H), 2.40–1.05 (m, 14H). FAB MS: 450 [M+1]$^+$

EXAMPLE 28

Preparation of N-(t-butoxycarbonyl)methyl-D-diphenylalanyl-L-prolyl-[(5-amidino-2-thienyl)methyl]amide.2AcOH

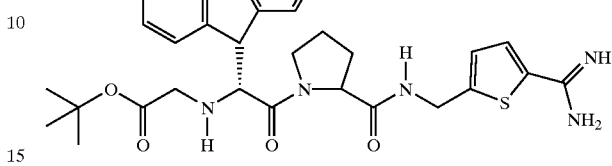

A) N-(t-Butoxycarbonyl)methyl-D-diphenylalanyl-L-prolyl-[(5-cyano-2-thienyl)methyl]amide To a cooled (0° C.) solution of D-Diphenylalanyl-L-prolyl-[(5-cyano-2-thienyl)methyl]amide.HCl prepared in Example 8, Step A (3.03 g, 6.06 mmol) in acetonitrile (60 mL) was added diisopropylethylamine (4.22 mL, 24.24 mmol) and t-butylbromoacetate (4.22 mL, 9.09 mmol), and the mixture stirred for 2 days at rt. After the reaction mixture was concentrated in vacuo, the residue was purified by column chromatography (EtOAc: n-hexane, 7:3) to give the title compound (2.51 g, 72%).

$^1$H NMR (CDCl$_3$) δ8.12 (t,1H), 7.37 (m, 5H), 7.19 (m, 5H), 6.93 (d, 1H), 4.61 (dd, 1H), 4.49 (dd, 1H), 4.25 (d, 2H), 4.12 (dd, 1H), 3.24 (s, 2H), 2.67 (m, 1H), 2.07 (m, 1H), 1.67 (m, 1H), 1.43 (m, 2H), 1.37 (s, 9H), 1.25 (m, 1H). FAB MS: 573[M+1]$^+$

B) N-(t-Butoxycarbonyl)methyl-D-diphenylalanyl-L-prolyl-[(5-hydroxyamidino-2-thienyl)methyl]amide To a solution of the compound obtained in Step A (2.31 g, 4.03 mmol) in a 4:1 mixture of ethanol and water (60 mL) was added hydroxylamine hydrochloride (1.04 g, 14.91 mmol) and sodium carbonate (726 mg, 6.85 mmol), and the mixture heated at reflux for 1 h. After the reaction mixture was concentrated in vacuo, the residue was diluted with EtOAc, washed with brine, dried over magnesium sulfate, and concentrated in vacuo to give the title compound (2.36 g, 96%).

$^1$H NMR (CD$_3$OD) δ8.13 (t, 1H), 7.42–7.35 (m, 4H), 7.27–7.11 (m, 6H), 7.01 (d, 1H), 6.83 (d, 1H), 4.87 (s, 1H), 4.56 (dd, 1H), 4.44 (dd, 1H), 4.27 (m, 3H), 3.25 (dd, 1H), 2.73 (m, 2H), 1.80–1.42 (m, 4H), 1.41 (s, 9H). FAB MS: 606 [M+1]$^+$

C) N-(t-Butoxycarbonyl)methyl-D-diphenylalanyl-L-prolyl-[(5-amidino-2-thienyl)methyl]amide.2AcOH The compound prepared in Step B (2.36 g, 3.89 mmol) was dissolved in methanol (45 mL). To this solution was added 10% palladium-on-carbon (240 mg), acetic anhydride (0.74 mL, 7.78 mmol) and the mixture was stirred for 8 h under H$_2$ (1 atm). The reaction mixture was filtered through Celite and the filtrate was concentrated in vacuo. The residue was purified by preparative HPLC H$_2$O-MeOH gradient) to give the title compound (1.6 g, 70%).

$^1$H NMR (CD$_3$OD) δ7.81 (d, 1H), 7.59 (d, 2H), 7.44 (t, 2H), 7.35–7.16 (m, 7H), 4.98 (d, 1H), 4.61 (s, 2H), 4.44 (d, 1H), 4.06 (m, 1H), 3.62 (q, 2H), 3.62 (dd, 1H), 2.91 (m, 1H), 1.77 (m, 3H), 1.47 (s, 9H), 1.35 (m, 1 H). FAB MS: 590 [M+1]$^+$

EXAMPLE 29

Preparation of N-carboxymethyl-D-diphenylalanyl-L-prolyl-[(5-amidino-2-thienyl)methyl]amide.2TFA

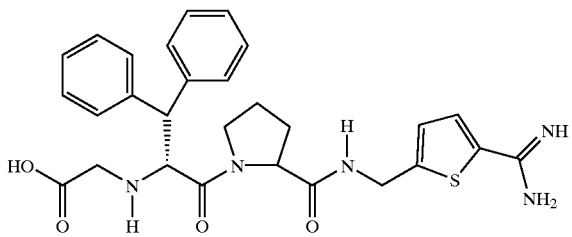

To a cooled (0° C.) solution of N-(t-butoxycarbonyl) methyl-D-diphenylalanyl-L-prolyl-[(5-amidino-2-thienyl)methyl]amide.2AcOH (1.4 g, 2.37 mmol, see Example 28) in dichloromethane (15 mL) was added TFA (15 mL) and the mixture stirred for 3.5 h. After the reaction mixture was concentrated in vacuo, the residue was purified by preparative HPLC (TFA (0.1%)-H$_2$O-MeOH gradient) to give the title compound (1.2 g, 80%).

$^1$H NMR (CD$_3$OD) δ7.80 (d, 1H), 7.62 (d, 2H), 7.48 (m, 2H), 7.39–7.22(m, 6H), 7.18 (d, 1H), 5.32 (d, 1H), 4.60 (dd, 2H), 4.58 (d, 1H), 4.06 (m, 1H), 3.84 (dd, 2H), 3.49 (m, 1H), 2.84 (m, 1H), 1.80 (m, 3H), 1.30 (m, 1H). FAB MS: 534[M+1]$^+$

EXAMPLE 30

Preparation of N-methyl-N-carboxymethyl-D-diphenylalanyl-L-prolyl-[(5-amidino-2-thienyl)methyl]amide.2TFA

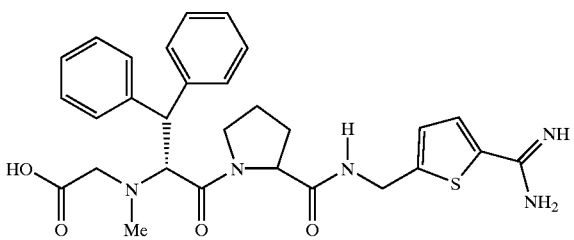

A) N-Methyl-N-(t-butoxycarbonyl)methyl-D-diphenylalanyl-L-prolyl-[(5-amidino-2-thienyl)methyl]amide.2TFA A solution of N-(t-butoxycarbonyl)methyl-D-diphenylalanyl-L-prolyl-[(5-cyano-2-thienyl)methyl]amide prepared in Example 28, Step A (0.18 g, 0.32 mmol) in pyridine (2 mL) was saturated with gaseous H$_2$S. After the mixture was allowed to stand for 1 day at rt, the solvent was removed in vacuo to obtain the thioamide as a yellow solid. To this material was added acetonitrile (2 mL) and iodomethane (0.2 mL, 3.15 mmol), and the mixture was heated at reflux for 4 h. After the solvent was evaporated in vacuo, the resulting methylthioamidate was dissolved in acetonitrile (2 mL). To this solution was added ammonium acetate (0.24 g, 3.15 mmol), and the mixture was heated at reflux for 2 h. The solution was cooled and concentrated and the residue purified by preparative HPLC (TFA(0.1%)-H$_2$O-MeOH gradient) to give the title compound (0.14 g, 64%).

$^1$H NMR (CD$_3$OD) δ7.79 (d, 1H), 7.50 (m, 2H), 7.41–7.10 (m, 9H), 5.01 (d, 1H), 4.70–4.40 (m, 3H), 4.02 (m, 1H), 3.59 (m, 1H), 3.37 (s, 2H), 3.20 (m, 1H), 2.91 (s, 3H), 1.78 (m, 3H), 1.56 (m, 10H) FAB MS: 604 [M+1]$^+$

B) N-Methyl-N-carboxymethyl-D-diphenylalanyl-L-prolyl-[(5-amidino-2-thienyl)methyl]amide.2TFA This compound was prepared from the compound obtained in Step A using the procedure described in Example 29; yield 64%.

$^1$H NMR (CD$_3$OD) δ7.81 (d, 1H), 7.62 (d, 1H), 7.43–7.12 (m, 10H), 5.22 (d, 1H), 4.69 (d, 1H), 4.61 (m, 2H), 3.93 (m, 1H), 3.71 (s, 2H), 3.50 (m, 1H), 3.13 (m, 1H), 2.84 (s, 3H), 1.81 (m, 3H), FAB MS: 548 [M+1]$^+$

EXAMPLE 31

Preparation of N-hydroxysulfonyl-D-diphenylalanyl-L-prolyl-[(5-amidino-2-thienyl)methyl]amide.TFA

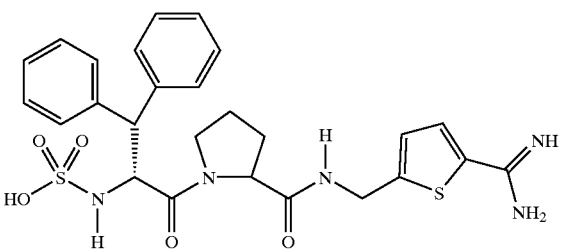

A) N-Hydroxysulfonyl-D-diphenylalanyl-L-prolyl-[(5-cyano-2-thienyl)methyl]amide. DIPA To a cooled (0° C.) solution of D-diphenylalanyl-L-prolyl-[(5-cyano-2-thienyl)methyl]amide.HCl (175 mg, 0.344 mmol) in dichloromethane (10 mL) was added chlorosulfonic acid (0.033 mL, 0.5 mmol) and diisopropylethylamine (DIPA, 0.226 mL, 1.3 mmol) and the mixture stirred for 3 h at rt. After the reaction was completed, the reaction mixture was diluted with dichloromethane, washed with 1N HCl and then with brine, dried over magnesium sulfate, and concentrated in vacuo to give the title compound (230 mg. 99%).

$^1$H NMR (CDCl$_3$) δ1.20–1.35 (m, 15H), 1.44 (m, 2H), 1.63 (m, 1H), 2.00 (m, 1 H), 2.62 (m, 1H), 2.91 (m, 2H), 3.44 (m, 2H), 3.80 (m, 1 H), 4.24 (d, 1H), 4.29 (d, 1H), 4.40–4.58 (m, 2H), 4.83 (d, 1H), 6.97 (d, 1H), 7.12–7.45 (m, 9H), 7.39 (d, 1H), 7.47 (m, 2H). FAB MS: 539 [M+1]$^+$

B) N-Hydroxysulfonyl-D-diphenylalanyl-L-prolyl-[(5-amidino-2-thienyl)methyl]amide.TFA To a solution of the compound prepared in Step A (230 mg) in ethanol (5 mL) was added hydroxylamine hydrochloride (74 mg, 1.03 mmol) and diisopropylamine (195 mg, 1.4 mmol) and the mixture stirred overnight at rt. The reaction mixture was concentrated in vacuo to give a white solid (380 mg). This solid was dissolved in methanol (5 mL) and 10% palladium-on-carbon (120 mg) and acetic acid (0.5 mL) were added. After the mixture was stirred for 36 h under H$_2$ (1 atm), the reaction mixture was filtered through Celite and the filtrate was concentrated in vacuo. The residue was purified by preparative HPLC (TFA (0.1%)-H$_2$O -MeOH gradient) to give the title compound (130 mg, 57%).

$^1$H NMR (CD$_3$OD) δ1.45–1.90 (m, 4H), 2.88 (m, 1H), 3.86 (m, 1H), 4.06 (m, 1H), 4.23 (d, 1H), 4.43 (m, 1H), 4.64 (m, 1H), 5.00 (d, 1H), 7.11–7.40 (m, 9H), 7.45 (m, 2H), 7.70 (d, 1H). FAB MS: 556 [M+1]$^+$

EXAMPLE 32

Preparation of N-methylsulfonyl-D-diphenylalanyl-L-azetidine-2-carboxyl-[(5-amidino-2-thienyl)methyl]amide.TFA

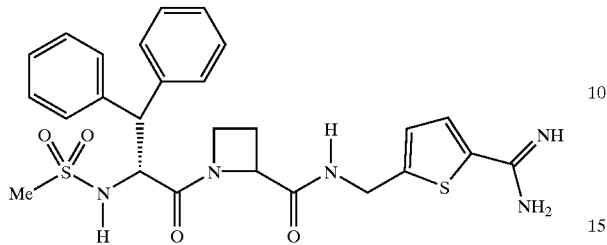

A) N-Boc-L-azetidine-2-carboxyl-[(5-cyano-2-thienyl)methyl]amide

To a cooled (0° C.) solution of N-Boc-L-2-azetidinecarboxylic acid (0.5 g, 4.94 mmol) in DMF (3 mL) was added 5-(aminomethyl)thiophene-2-carbonitrile.HCl (0.48 g, 2.74 mmol), EDC (0.62 g, 3.24 mmol), HOBT (0.40 g, 2.99 mmol), and triethylamine (1.04 mL, 7.47 mmol) and the mixture stirred for 2 h at rt. The solvent was removed in vacuo and the residue dissolved in EtOAc, washed sequentially with a saturated sodium bicarbonate solution, 1N HCl, and brine. After the solution was dried over magnesium sulfate and concentrated in vacuo, the residue was purified by column chromatography (EtOAc: n-hexane, 2:1) to give the title compound (0.54 g, 68%).

$^1$H NMR (CDCl$_3$) δ7.46 (d, 1H), 6.97 (d, 1H), 4.75–4.50 (m, 3H), 3.92 (m, 1H), 3.79 (m, 1H), 2.52–2.40 (m, 2H), 1.42 (s, 9H). FAB MS: 322 [M+1]$^+$

B) N-Boc-D-diphenylalanyl-L-azetidine-2-carboxyl-[(5-cyano-2-thienyl)methyl]amide To a cooled (0° C.) solution of the compound prepared in Step A (1.4 g, 2.37 mmol) in dichloromethane (15 mL) was added TFA (15 mL) and the mixture stirred for 3 h at rt. The resulting solution was concentrated in vacuo to give Boc-deprotected compound as TFA salt (0.52 g, 93%). This product (0.2 g, 0.6 mmol) was dissolved in DMF (6 mL), and to this solution was added Boc-D-diphenylalanine (0.18 g, 0.54 mmol), EDC (0.13 g, 0.7 mmol), HOBT (0.09 g, 0.54 mmol). The mixture was stirred until clear and then cooled to 0° C. After triethylamine was added (0.3 mL, 2.16 mmol), the resulting mixture was stirred for additional 2 h at rt. The solvent was removed in vacuo and the residue dissolved in EtOAc, washed sequentially with a saturated sodium bicarbonate solution, 1N HCl, and brine. After the solution was dried over magnesium sulfate and concentrated in vacuo, the residue was purified by column chromatography (EtOAc: n-hexane, 2:1) to give the title compound (0.2 g, 69%).

$^1$H NMR (CDCl$_3$) δ8.30 (bs, 1H), 7.45–7.14 (m, 11H), 6.96 (d, 1H), 4.83 (bs, 1H), 4.67–4.48 (m, 3H), 4.43 (m, 1H), 4.32 (m, 1H), 4.04 (m, 1H), 2.97 (m, 1H), 2.21 (m, 1H), 2.02 (m, 1H), 1.28 (s, 9H). FAB MS: 545 [M+1]$^+$

C) N-Methylsulfonyl-D-diphenylalanyl-L-azetidine-2-carboxyl-[(5-amidino-2-thienyl)methyl]amide.TFA This compound was prepared from the compound obtained in Step B using the same procedure as described in Example 8 except that methanesulfonylchloride was used instead of methylchloroformate; yield 47%.

$^1$H NMR (CD$_3$OD) δ7.78 (d, 1H), 7.45–7.18 (m, 11H), 4.65 (d, 1H), 4.61 (s, 2H), 4.34–4.19 (m, 3H), 3.48 (m, 1H), 2.81 (s, 3H), 2.09 (m, 2H). FAB MS: 540 [M+1]$^+$

EXAMPLE 33

Preparation of N-methylsulfonyl-D-diphenylalanyl-L-prolyl-[(4-amidino-5-methyl-2-thienyl)methyl]amide.TFA

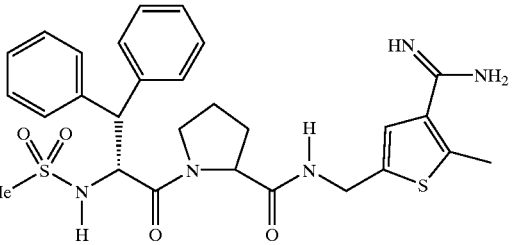

A) 5-Aminomethyl-2-methylthiophene-3-carbonitrile.HCl

This compound was prepared from 4-bromo-5-methylthiophene-2-carboxaldehyde using the procedure described in Example 11, Step A through D; yield 22%.

$^1$H NMR(CD$_3$OD) δ2.59 (s, 3H), 4.52 (s, 2H), 7.00 (s, 1H), 7.25 (s, 1H). FAB MS: 153 [M+1]$^+$

B) N-methylsulfonyl-D-diphenylalanyl-L-prolyl-[(4-amidino-5-methyl-2-thienyl)methyl]amide.TFA This compound was prepared from N-methylsulfonyl-D-diphenylalanyl-L-proline (Example 3, Step A) and 2-aminomethyl-5-methylthiophene-4-carbonitrile.HCl using the procedure described in Example 1, Step E and F; yield 38%.

$^1$H NMR (CD$_3$OD) δ1.48 (m, 1H), 1.62 (m, 1H), 1.90 (m, 2H), 2.65 (s, 2H), 2.90–3.03 (m, 4H), 3.62 (m, 1H), 4.02 (m, 1H), 4.34 (d, 1H), 4.52 (m, 2H), 5.11 (m, 1H), 7.19–7.56 (m, 11H). FAB MS: 568 [M+1]$^+$

EXAMPLE 34

Preparation of N-methylsulfonyl-D-diphenylalanyl-L-prolyl-[(5-amidino-2-furanyl)methyl]amide.TFA

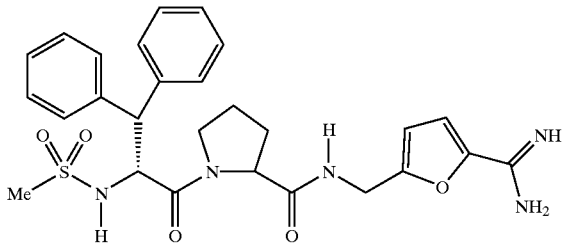

This compound was prepared from N-methylsulfonyl-D-diphenyalalanyl-L-proline (see Example 3, Step A) and 5-(aminomethyl)furan-2-carbonitrile.HCl using the procedure described in Example 1, Step E and F; yield 20%.

$^1$H NMR (CD$_3$OD) δ7.48(m, 3H), 7.35 (m, 2H), 7.25 (m, 6H), 6.62(d, 1H), 5.02 (d, 1H), 4.44 (m, 2H), 4.32 (d, 2H), 4.02(dd, 1H), 3.71 (m, 1H), 2.93 (m, 1 H), 2.85(s, 3H), 1.79–1.39 (m, 4H). FAB MS: 538 [M+1]$^+$

EXAMPLE 35

Preparation of N-methoxycabonyl-D-diphenylalanyl-L-prolyl-[(5-amidino-2-furanyl)methyl]amide.TFA

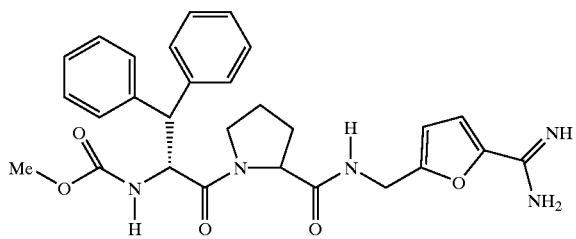

This compound was prepared from N-Boc-D-diphenylalanyl-L-proline and 5-(aminomethyl)furan-2-carbonitrile.HCl using the procedures described in Example 7, Step A and Example 8; yield 35%.

$^1$H NMR (CD$_3$OD) δ7.49(d, 1H), 7.39 (d, 2H), 7.34 (t, 2H), 7.25 (m, 6H), 6.57(d, 1H), 5.15 (d, 1H), 4.59 (d, 1H), 4.37 (dd, 2H), 4.05(dd, 1H), 3.85 (m, 1H), 3.39 (s, 3H), 2.89(m, 1H), 1.82–1.46 (m, 4H). FAB MS: 518 [M+1]$^+$

EXAMPLE 36

Preparation of N-aminosulfonyl-D-diphenylalanyl-L-prolyl-[(5-amidino-3-furanyl)methyl]amide.TFA

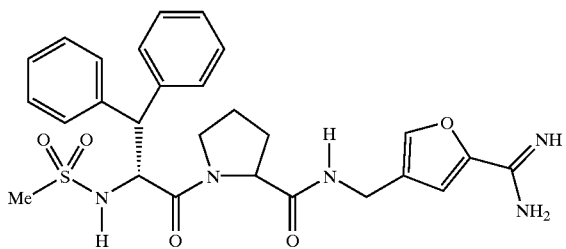

A) 4-(Aminomethyl)furan-2-carbonitrile.HCl

This compound was prepared from 2-bromo-4-(hydroxymethyl)furan (see Acta. Chemica. Scandinavica. 1991, 45, 914) using the procedure described in Example 11, Step B through D; yield 61%.

$^1$H NMR (CD$_3$OD) δ7.54 (s, 1H), 7.12 (s, 1H), 4.32 (s, 2H). FAB MS: 159 [M+1]$^+$

B) N-aminosulfonyl-D-diphenylalanyl-L-prolyl-[(5-amidino-3-furanyl)methyl]amide.TFA This compound was prepared from N-aminosulfonyl-D-diphenylalanyl-L-proline (see Example 1, Step D) and 4-(aminomethyl)furan-2-carbonitrile.HCl using the procedure described in Example 1, Step E and F; yield 36%.

$^1$H NMR (CD$_3$OD) δ7.83 (s, 1H), 7.47(s, 1H), 7.43 (d, 2H), 7.35 (t, 2H), 7.25 (m, 6H), 4.93 (d, 1H), 4.31 (d, 2H), 4.11 (dd, 1H), 4.02 (dd, 1H), 3.75 (m, 1H), 288 (m, 1H), 1.84–1.45 (m, 4H). FAB MS: 539 [M+1]$^+$

EXAMPLE 37

Preparation of N-aminosulfonyl-D-diphenylalanyl-L-prolyl-[(4-amidino-2-thiazolyl)methyl]amide.TFA

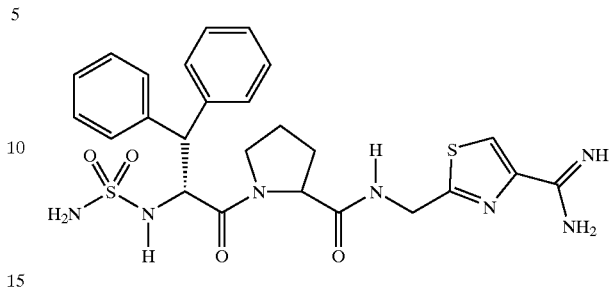

A) 2-(Aminomethyl)thiazole-4-carbonitrile.HCl

To a cooled (0° C.) solution of 2-(N-Boc-aminomethyl)thiazole-4-carboxamide (200 mg, 0.78 mmol, see Angew. Chem. Int. Ed. Engl. 1996, 35,1503) in dichloromethane (7 mL) was added triethylamine (0.32 mL, 2.34 mmol) and acetic anhydride (0.22 mL, 1.56 mmol) and the mixture stirred for 1 h. After the solvent was removed, the residue was purified by column chromatography (EtOAc: n-hexane, 3:7). 2-(N-Boc-aminomethyl)thiazole-4-carbonitrile (150 mg, 0.627 mmol) thus obtained was dissolved in methanol (10 mL) and cooled to 0° C. To this was added dropwise acetylchloride (30 equivalent) and the mixture stirred for 1 h at rt. The solvent was removed in vacuo to give the title compound (90 mg, 81%).

$^1$H NMR (CD$_3$OD) δ7.94 (s, 1H), 5.44 (s, 1H), 4.59 (s, 2H). FAB MS: 176 [M+1]$^+$

B) N-aminosulfonyl-D-diphenylalanyl-L-prolyl-[(4-amidino-2-thiazolyl)methyl]amide.TFA This compound was prepared from N-aminosulfonyl-D-diphenylalanyl-L-proline (see Example 1, Step D) and 2-(aminomethyl)thiazole-4-carbonitrile.HCl using the procedure described in Example 1, Step E and F; yield 48%.

$^1$H NMR (CD$_3$OD) δ8.56 (s, 1H), 7.45(d, 2H), 7.35(t, 2H), 7.25 (m, 6H), 4.95 (d, 1H), 4.67 (m, 2H), 4.34 (d, 1H), 4.11 (dd, 1H), 3.78 (m, 1H), 2.89 (m, 1H), 1.90–1.45 (m, 4H).

FAB MS: 556 [M+1]$^+$

EXAMPLE 38

Preparation of N-methylsulfonyl-D-diphenylalanyl-L-prolyl-[(5-amidino-1-methyl-2-pyrrolyl)methyl]amide.TFA

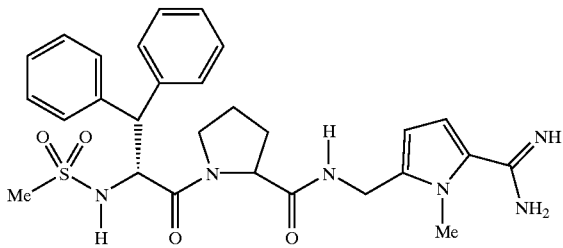

This compound was prepared from N-methylsulfonyl-D-diphenylalanyl-L-proline (see Example 3, Step A) and 5-(aminomethyl)-1-methylpyrrole-2-carbonitrile using the procedure described in Example 1, Step E and F; yield 17%. 5-(Aminomethyl)-1-methyl-pyrrole-2-carbonitrile was prepared from 1,5-dimethyl-pyrrole-2-carbonitrile using the procedure described in Example 1, Step A and B.

$^1$H NMR (CD$_3$OD) δ1.40 (m, 1H), 1.65 (m, 1H), 1.84 (m, 2H), 2.81 (s, 3H), 2.97 (m, 1H), 3.69 (s, 3H), 3.78 (m, 1H), 4.02 (m, 1H), 4.30 (d, 1H), 4.56 (m, 2H), 5.00 (m, 1H), 6.22 (d, 1H), 6.88 (d, 1H), 7.23–7.50 (m, 9H), 7.65 (m, 1H) FAB MS: 551 [M+1]$^+$

EXAMPLE 39

Preparation of N-carboxymethyl-D-diphenylalanyl-L-prolyl-[(5-amidino-3-thienyl)methyl]amide.2TFA

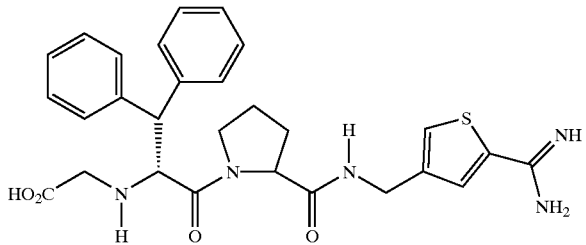

This compound was prepared from D-diphenylalanyl-L-prolyl-[(5-cyano-3-thienyl)methyl]amide.HCl (obtained during the preparation of Example 19) using the procedures described in Examples 28 and 29; yield 41%.

$^1$H NMR (CD$_3$OD) δ7.91 (s, 1H), 7.88 (s, 1H), 7.67(d, 2H), 7.50 (t, 2H), 7.38–7.25 (m, 6H), 5.34 (d, 1H), 4.58(d, 1H), 4.42 (dd, 2H), 4.07 (dd, 1H), 3.78 (dd, 2H), 3.53 (m, 1H), 2.89(m, 1H), 1.83–1.72 (m, 3H), 1.31 (m, 1H). FAB MS: 534 [M+1]$^+$

EXAMPLE 40

Preparation of N-carboxymethyl-D-diphenylalanyl-L-prolyl-[(4-amidino-2-thiazolyl)methyl]amide.2TFA

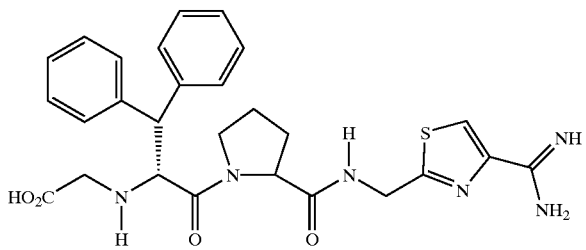

A) D-Diphenylalanyl-L-prolyl-[(4-cyano-2-thiazolyl)methyl]amide.HCl

This compound was prepared from 2-(aminomethyl)thiazole-4-carbonitrile.HCl (see Example 37, Step A) using the procedures described in Example 7, Step A and Example 8, Step A.

$^1$H NMR (CDCl$_3$) δ8.56 (s,1H), 7.54–7.23 (m, 10H), 4.77 (d, 1H), 4.57 (d, 1H), 4.55 (dd, 1H), 4.23 (m, 2H), 3.77 (m, 1H), 2.41 (m, 1H), 1.94 (m, 1H), 1.62–1.35 (m, 3H).

FAB MS: 460 [M+1]$^+$

B) N-carboxymethyl-D-diphenylalanyl-L-prolyl-[(4-amidino-2-thiazolyl)methyl]amide.2TFA This compound was prepared from the compound obtained in Step A using the procedures described in Examples 28 and 29; yield 35% overall.

$^1$H NMR (CD$_3$OD) δ8.63(s,1H), 7.65 (d, 2H), 7.52 (t, 2H), 7.45–7.23 (m, 6H), 5.31(d, 1H), 4.74(s, 2H), 4.55 (d, 1H), 4.13 (m, 1H), 3.78 (dd, 2H), 3.52 (m, 1H), 2.86 (m, 1H), 1.81 (m, 3H), 1.37 (m, 1H) FAB MS: 535 [M+1]$^+$

EXAMPLE 41

Preparation of N-(2-carboxyethyl)-D-diphenylalanyl-L-prolyl-[(5-amidino-2-thienyl)methyl]amide.2TFA

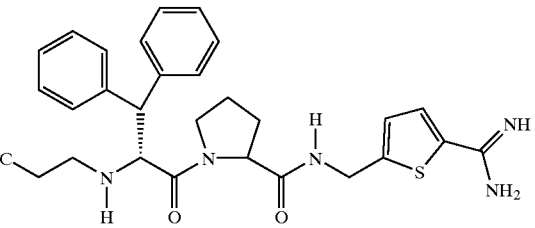

A) N-[2-(methoxycarbonyl)ethyl]-D-diphenylalanyl-L-prolyl-[(5-cyano-2-thienyl)methyl]amide A mixture of D-Diphenylalanyl-L-prolyl-[(5-cyano-2-thienyl)methyl]amide.HCl (400 mg, 0.81 mmol, prepared in Example 8, Step A), sodium carbonate (690 mg, 6.5 mmol), sodium iodide (609 mg, 4.065 mmol), tetrabutylammonium bromide (79 mg, 0.244 mmol), and methyl 3-bromopropionate (0.2 mL, 1.626 mmol) in toluene (8 mL) was heated at reflux for 5 h. The reaction mixture was concentrated in vacuo and the residue purified by column chromatography (EtOAc: n-hexane, 7:3) to give the title compound (180 mg, 41%).

$^1$H NMR (CDCl$_3$) δ7.97 (t, 1H), 7.42 (d, 1H), 7.38–7.13 (m, 10 H), 6.93 (d, 1H), 4.52(dd, 2H), 4.31 (d, 1H), 4.22 (dd, 1H), 4.14 (dd, 1H), 3.61 (s, 1H), 3.44 (m, 1H), 2.87 (m, 1H), 2.70 (m, 2H), 2.34 (m, 2H), 2.23 (m, 1H), 1.82 (m, 1H), 1.53 (m, 1H), 124(m, 1H).

FAB MS: 545 [M+1]$^+$

B) N-[2-(methoxycarbonyl)ethyl]-D-diphenylalanyl-L-prolyl-[(5-amidino-2-thienyl)methyl]amide.2AcOH This compound was prepared from the compound obtained in Step A (160 mg) using the procedure described in Example 28, Step B and C; yield 54%.

$^1$H NMR (CD$_3$OD) δ7.74 (d, 1H), 7.35–7.11 (m, 10H), 6.98 (d, 1H), 4.72 (dd, 1H), 4.30 (dd, 1H), 4.17(s, 2H), 4.16 (dd, 1H), 3.53 (s, 3H), 3.52 (m, 1H), 2.89 (m, 2H), 2.75 (m, 1H), 2.38 (m, 2H), 1.89 (m, 2H), 1.62 (m, 1H), 1.40(m, 1 H). FAB MS: 562 [M+1]$^+$

C) N-(2-Carboxyethyl)-D-diphenylalanyl-L-prolyl-[(5-amidino-2-thienyl)methyl]amide.2TFA A mixture of the compound prepared in Step B (91 mg, 0.16 mmol), 0.5N LiOH (10 mL), and water (3 mL) was stirred for 3 h at rt. The reaction mixture was neutralized with 1N HCl and concentrated in vacuo. The residue was purified by preparative HPLC (TFA (0:1%)-H$_2$O-MeOH gradient) to give the title compound (55 mg, 44%).

$^1$H NMR (CD$_3$OD) δ7.81 (d, 1H), 7.62 (d, 2H), 7.50 (t, 2H), 7.42–7.32(m, 6H), 7.21 (d, 1H), 5.12 (d, 1H), 4.61(dd, 2H), 4.50 (d, 1H), 4.11 (m, 1H), 3.60 (m, 1H), 2.78 (m, 1H), 2.68(m, 2H) 1.83 (m, 3H), 1.30 (m, 1H). FAB MS: 548 [M+1]$^+$

EXAMPLE 42

Preparation of N-Boc-D-Diphenylalanyl-L-prolyl-[(5-amidrazono-2-thienyl)methyl]amide.TFA

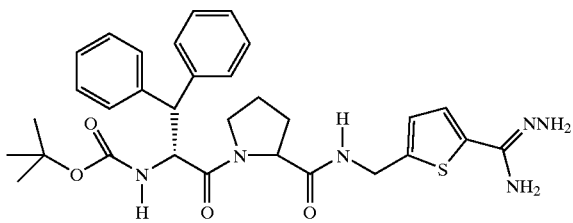

This compound was prepared from N-Boc-D-diphenylalanyl-L-prolyl-[(5-amidino-2-thienyl)methyl]amide (Example 7, Step A) using the procedure described in Example 4.

$^1$H NMR (CD$_3$OD) δ7.67 (d, 1H), 7.49–7.17 (m, 10H), 7.12 (d, 1H), 5.10 (d, 1H), 4.60 (dd, 2H), 4.33 (d, 1H), 4.07 (m, 1H), 3.80 (m, 1H), 2.93 (m, 1H), 1.89–1.73 (m, 2H), 1.58 (m, 1H), 1.47 (m, 1H), 1.29 (s, 9H).

EXAMPLE 43

Preparation of D-diphenylalanyl-L-prolyl-[(5-amidrazono-2-thienyl)methyl]amide.2TFA

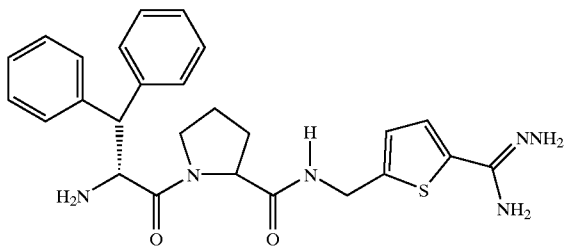

To a solution of the compound obtained in Step A (0.05 g, 0.071 mmol) in methanol was added 0.4N HCl solution in methanol (0.9 mL) and the mixture stirred for 2 h. The solvent was removed in vacuo and the residue was purified by preparative HPLC (TFA (0.1%)-H$_2$O-MeOH gradient) to give the title compound (45 mg, 88%).

$^1$H NMR (CD$_3$OD) δ7.69 (d, 1H), 7.59 (m, 2H), 7.47 (m, 2H), 7.40 (m, 2H), 7.30 (m, 4H), 7.19 (d, 1H), 5.10 (d, 1H), 4.61 (dd, 2H), 4.45 (d, 1H), 4.07 (m, 1H), 3.58 (m, 1H), 2.82 (m, 1H), 1.78 (m, 3H), 1.33 (m, 1H).

EXAMPLE 44

Preparation of N-methylsulfonyl-D-phenylalanyl-L-prolyl-[(5-amidrazono-2-thienyl)methyl]amide.TFA

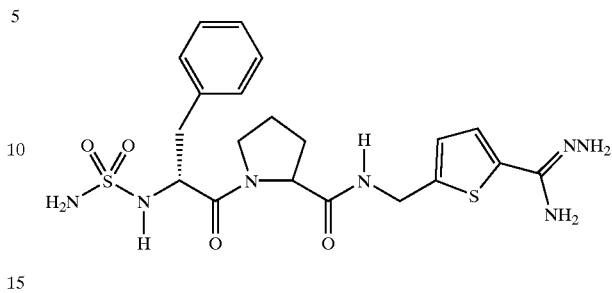

The title compound was prepared from D-phenylalanyl-L-proline methyl ester.HCl using the procedures described in Example 7, Step A and B, followed by Example 4.

$^1$H NMR (CD$_3$OD) δ8.52 (m, 1H), 7.72 (d, 1H), 7.19 (d, 1H), 4.58 (m, 2H), 4.41 (dd, 1H), 4.31 (m, 1H), 3.85 (m, 1H), 3.58 (m, 1H), 2.87 (s, 3H), 2.28–0.85 (m, 17H).

EXAMPLE 45

In vitro Enzyme Assays for Determining Inhibition Constants

The activity of thrombin was measured spectrophotometrically using tosyl-Gly-Pro-Arg-p-nitroanilide acetate (Chromozym TH, Boehringer Mannheim) as a substrate. Thrombin used in this test was prepared from human plasma according to the protocol of Ngai and Chang (see, Biochem. J. 1991, 280, 805). Each compound was dissolved in DMSO to make a 1 mM stock solution and dilutions were made thereof with assay buffer (0.1 M TrisHCl, 0.15 M NaCl, 0.1% polyethylene glycol 8000, pH 7.8). Different concentrations of inhibitor were mixed with 0.3 NIH units of thrombin in 0.8 mL of the buffer. The mixture was incubated for 10 min at room temperature before adding 0.2 mL of the substrate to a final concentration of 20 μM. The release of p-nitroaniline by hydrolysis of the substrate was monitored for 5 min by measuring the increase in optical density at 381 nm with a UV2100S spectrometer (Shimadzu). A graph for the reciprocal value of initial velocity to the inhibitor concentration was derived from progress curves by fitting the data using a linear regression program. The inhibition constants (Ki values) were then obtained from the Dixon plot equation (see, Biochem. J. 1953, 55, 170). Under these conditions, the Km value for the substrate hydrolysis was 5.2 μM as determined from a non-linear regression analysis of initial rate assuming Michaelis-Menten kinetics.

In certain studies with highly potent inhibitors (Ki<0.1 nM) where the degree of thrombin inhibition was very high, a more sensitive assay was employed. In this assay, the concentration of Chromozym TH and thrombin was set to 80 μM and 1.5 mU/mL, respectively, and the hydrolysis reaction was monitored for 1.5 hr.

Table 1 shows the thrombin inhibitory activity (Ki values) obtained with the exemplary compounds of the present invention. It can be identified that the compounds of the present invention show excellent inhibitory activity against thrombin.

EXAMPLE 46

Pharmacokinetic Studies for Determining Oral Bioavailability

Male Sprague-Dawley rats (250–300 g) were restrained individually in a surgical plate (Dae Jong Instrument Company, Seoul, Korea) as supine position. The femoral artery and the femoral vein (iv only) of rats were cannulated with polyethylene tubing (PE-50, Clay Adams, Parsippany, N.J., USA) under light ether anesthesia. After complete recovery from anesthesia, rats were given 30 mg/kg of test compound dissolved in distilled water via oral gavage or given 10 mg/kg via the femoral vein for intravenous (iv) study. Blood samples (0.25 mL) were collected from the femoral artery at 0 (for control), 1 (iv only), 5, 15, 30, 60, 90 (iv only), 120, 180, and 240 min after dosing.

Male beagle dogs (7–10 kg, Hazleton Research Product Inc., Kalamazoo, Mich., USA) were housed individually in a metabolic cage for plasma disposition study. Dogs were orally administered with 10 mg/kg of test compound dissolved in distilled water via gavage or injected with 2 mg/0.2 mL/kg via the cephalic vein using INTROCAN®. Blood samples were withdrawn via the cephalic vein at 0 (for control), 1, 5 (iv only), 15, 30, 60, 90, 120, 180, 240, 360 (po only) and 480 (po only) min after dosing.

Blood samples were taken into heparinized tube (25 U/mL), deproteinized with 2 volumes of methanol, and centrifuged. The resulting supernatant (60 µL) was analyzed by HPLC eluting with a mixture of 0.1% trifluoroacetic acid aqueous solution and acetonitrile with a ratio of 81% to 19%. Plasma concentration of test compound was recorded and used to calculate the pharmacokinetic parameters: maximum plasma concentration of test compound ($C_{max}$), time of maximum plasma concentration ($T_{max}$) area under the curve (AUC), and fraction of test compound absorbed (F).

The compounds of the present invention demonstrate generally good oral absorption in rats and dogs. In particular, the compounds bearing D-diphenylalaine moiety exhibit higher absorption compared to the corresponding compounds that contain D-cyclohexylalanine moiety. Table 2 illustrates the pharmacokinetic results for some exemplary compounds of invention obtained upon oral dosing in rats.

EXAMPLE 47

In vivo Studies of the Compounds Claimed Herein Were Conducted Using the Following Procedure Male Sprague-Dawley rats (body weights 250–300 g, 3–4/group) were anaesthetized by intraperitoneal injection with urethane solution (1.25 g/kg). The abdomen was surgically opened by a midline incision and the inferior venae cava was carefully dissected free from surrounding connective tissue. The venae iliolumbar and spermatica were ligated with a silk thread. Thrombus formation was initiated by infusion of a thromboplastin preparation (Simplastin®) using an infusion pump (Model 100, IITC Life Science, USA) via the left femoral vein at 0.5 mL/kg/min. Simplastin® (Organon Teknika, USA) was reconstituted with 4 mL of distilled water and then given diluted at 1:2.5 in distilled water. At the start of infusion for 30 seconds, the vena cava was ligatured below the left renal vein. After the end of infusion, vena cava was also ligatured above the iliac veins 16 mm apart from upper ligature. After 15 min of stasis, the thrombus formed inside the vessel was carefully removed and weighed. Before wighing, the excess blood was removed by blotting the wet clot on the wet Whatman filter paper (see, Millet, J.; Theveniaux, J.; Brown, N. L. Thromb. Haemost. 1992, 67, 176).

Saline (control) or test compounds (1 mg/kg) were injected as a bolus via the femoral vein starting 5 min before the thromboplastin infusion. Bolus injection volume was 0.5 mL/kg. Antithrombotic activity was expressed as a percentage where:

Antithrombotic activity $(\%) = 100 \times (A-B)/A$

A = mean clot weight of control group
B = mean clot weight of test compound group The results shows that the compounds of the present invention are effective in preventing thrombotic occlusions. In particular, the compounds containing both D-diphenylalaine and amidine moieties exhibit excellent antithrombotic activity. For example, at a dose of 1 mg/kg, the compounds of Example 1, 3,11, 15, 19, 29, and 41, are 100% effective in inhibiting thrombus formation in the rat venous thrombosis model.

TABLE 1

| Example | Ki (nM) |
|---|---|
| 1 | 0.003 |
| 2 | 4.7 |
| 3 | 0.004 |
| 4 | 0.53 |
| 5 | 5.80 |
| 6 | 0.021 |
| 7 | 0.007 |
| 8 | 0.014 |
| 9 | 0.065 |
| 10 | 0.052 |
| 11 | 0.022 |
| 12 | 0.040 |
| 13 | 0.073 |
| 14 | 0.17 |
| 15 | 0.056 |
| 16 | 0.045 |
| 17 | 0.41 |
| 18 | 6.21 |
| 19 | 0.060 |
| 20 | 0.011 |
| 21 | 0.017 |
| 22 | 0.02 |
| 23 | 0.03 |
| 24 | 0.024 |
| 25 | 0.053 |
| 26 | 4.6 |
| 27 | 13.7 |
| 28 | 0.062 |
| 29 | 0.015 |
| 30 | 0.003 |
| 31 | 0.10 |
| 32 | 0.053 |
| 33 | 0.12 |
| 34 | 1.4 |
| 35 | 4.6 |
| 36 | 0.013 |
| 37 | 0.12 |
| 38 | 0.23 |
| 39 | 0.20 |
| 40 | 0.60 |
| 41 | 0.011 |
| 42 | 84 |
| 43 | 9.1 |
| 44 | 395 |

TABLE 2

Pharmacokinetic parameters after oral dosing in rats (30 mg/kg)

| Example | $C_{max}$ (µg/mL) | $T_{max}$ (min) | AUC (µg.min/mL) |
|---|---|---|---|
| 1 | 2.2 | 60 | 253 |
| 5 | 1.8 | 32 | 280 |
| 8 | 9.6 | 60 | 1615 |
| 11 | 2.1 | 45 | 254 |
| 14 | 4.5 | 80 | 850 |
| 19 | 5.2 | 80 | 1297 |
| 29 | 9.5 | 15 | 1390 |
| 35 | 7.1 | 45 | 965 |

TABLE 2-continued

Pharmacokinetic parameters after oral dosing in rats (30 mg/kg)

| Example | $C_{max}$ (μg/mL) | $T_{max}$ (min) | AUC (μg.min/mL) |
|---|---|---|---|
| 39 | 4.6 | 15 | 212 |
| 40 | 11.1 | 25 | 1126 |
| 41 | 4.9 | 20 | 503 |

All the documents cited herein, including the foreign priority documents, are hereby incorporated by reference.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not be the above description, but by the following claims and their equivalents.

What is claimed is:

1. A compound having formula I:

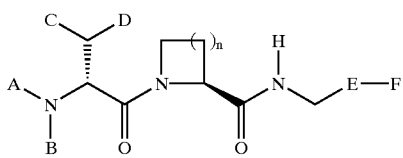

(I)

and pharmaceutically acceptable salts thereof
wherein
n is 2
A is hydrogen, alkyl, $C_{3-7}$ cycloalkyl, aryl, —$SO_2R^1$, —$SO_3R^1$, —$COR^1$, —$CO_2R^2$, —$PO(OR^1)_2$,—$(CH_2)_m CO_2R^1$, —$(CH_2)_m SO_2R^1$, —$(CH_2)_m SO_3R^1$, or —$(CH_2)_m PO(OR^1)_2$,
wherein
$R^1$ is hydrogen, $C_{1-6}$ alkyl, $C_{3-7}$ cycloalkyl, aryl, —$(CH_2)_m$aryl, or —$NR^3R^4$, and
$R^2$ is $C_{1-6}$ alkyl, $C_{3-7}$ cycloalkyl, aryl, —$(CH_2)_m$aryl, or alkenyl,
m is 1, 2, or 3,
wherein
aryl is unsubsituted or substituted phenyl or 5–6 membered aromatic heterocyclic ring,
$R^3$ and $R^4$ are independently hydrogen, $C_{1-6}$ alkyl, or $C_{3-7}$ cycloalkyl, and B is hydrogen or $C_{1-6}$ alkyl, and C and D are independently
hydrogen,
phenyl unsubsituted or substituted with one or two substituents selected from $C_{1-4}$ alkyl, $C_{1-4}$ alkoxy, $CF_3$, methylenedioxy, halogen, hydroxy, or —$NR^3R^4$,
a 5–6 membered heterocyclic ring system which may be saturated or unsaturated, and which consists of carbon atoms and 1–3 heteroatoms selected from the group consisting of N, O, and S, or
C and D are $C_{4-7}$ cycloalkyl; and E is

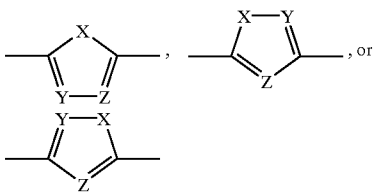

wherein
X is S, O, or NR5,
Y and Z are independently N or $CR^6$,
wherein
$R^5$ is hydrogen or $C_{1-4}$ alkyl and
$R^6$ is hydrogen, halogen, $CF_3$ or $C_{1-4}$ alkyl, and
F is —$C(NH)N(R^7)_2$, —$C(NH_2)NN(R^7)_2$,—$C(NH_2)NOH$, or -$CH_2NH(R^7)_2$
wherein $R^7$ is the same or different,
$R^7$ is hydrogen, $C_{1-4}$ perfluoroalkyl or $C_{1-4}$ alkyl.

2. The compound of claim 1 where C and D are independently selected from the group consisting of:
phenyl unsubsituted or substituted with one or two substituents selected from $C_{1-4}$ alkyl, $C_{1-4}$ alkoxy, methylenedioxy, halogen, hydroxy, or $NR^3R^4$, wherein $R^3$ and $R^4$ are as previously defined,
$C_{3-5}$ or $C_7$ cycloalkyl, or
a 5–6 membered heterocyclic ring system which may be saturated or unsaturated, and which consists of carbon atoms and 1–3 heteroatoms selected from the group consisting of N, O, and S, and
both C and D are $C_{3-7}$ cycloalkyl.

3. The compound of claim 1, wherein A is selected from the group consisting of hydrogen, aryl, —$SO_2R^1$, —$SO_3H$, —$COR^1$, —$CO_2R^2$, —$PO(R^1)_2$ —$PO(OR^1)_2$, and —$(CH_2)_m CO_2R^1$, wherein $R^1$ and $R^2$ are as previously defined.

4. The compound of claim 3, wherein A is selected from the group consisting of —$SO_2NR^3R^4$, —$PO(R^1)_2$, —$PO(OR^1)_2$, —$(CH_2)_m CO_2R^1$, and aryl, wherein $R^1$, $R^3$ and $R^4$ are as previously defined.

5. The compound of claim 2, wherein A is selected from the group consisting of hydrogen, —$SO_2R^1$, —$PO(C_{1-6} alkyl)_2$, —$PO(OC_{1-6} alkyl)_2$, —$CO(C_{1-6}$ alkyl), —$CO_2R^2$, —$(CH_2)_m CO_2H$, and —$(CH_2)_m CO_2(C_{1-6}$ alkyl),
wherein
m is 1 or 2, and
$R^1$ is $C_{1-6}$ alkyl, aryl, —$(CH_2)_m$aryl, hydroxy, or —$NR^3R^4$,
wherein $R^3$ and $R^4$ are as previously defined.

6. The compound of claim 2 where C and D are independently selected from the group consisting of:
phenyl, pyridyl, and
both C and D are cyclohexyl unsubsituted or substituted with one or two substituents selected
from $C_{1-4}$ alkyl, $C_{1-4}$ alkoxy, methylenedioxy, halogen, hydroxy, or $NR^3R^4$.

7. The compound of claim 2 where C and D are independently selected from the group consisting of:
phenyl and both C and D are cyclohexyl.

8. The compound of claim 1, wherein E is selected from the group consisting of:

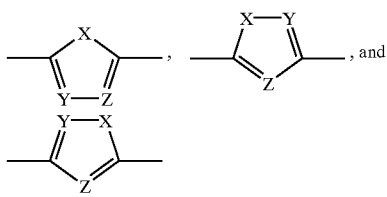

wherein
when X is S, O, or NR$^5$, Y is CH and Z is CR$^6$, or Y is CR$^6$ and Z is CH, or
when X is S, O, or NH, Y is N and Z is CR$^6$, or Y is CR$^6$ and Z is N,
wherein R$^5$ and R$^6$ are as previously defined.

9. The compound of claim 8, wherein
R$^5$ and R$^6$ are independently hydrogen or C$_{1-4}$ alkyl.

10. The compound of claim 1, wherein F is selected from the group consisting of: —C(NH)NH$_2$, —C(NH$_2$)NOH, —C(NH$_2$)NNH$_2$, and —CH$_2$NH$_2$.

11. The compound as defined in claim 1 where the compound is selected from the group consisting of:

N-aminosulfonyl-D-diphenylalanyl-L-prolyl-[(5-amidino-2-thienyl)methyl]amide,
N-aminosulfonyl-D-diphenylalanyl-L-prolyl-[(5-aminomethyl-2-thienyl)methyl]amide,
N-methylsulfonyl-D-diphenylalanyl-L-prolyl-[(5-amidino-2-thienyl)methyl]amide,
N-methylsulfonyl-D-diphenylalanyl-L-prolyl-[(5-amidrazono-2-thienyl)methyl]amide,
N-methylsulfonyl-D-diphenylalanyl-L-prolyl-[(5-aminomethyl-2-thienyl)methyl]amide,
N-benzylsulfonyl-D-diphenylalanyl-L-prolyl-[(5-amidino-2-thienyl)methyl]amide,
N-t-butoxycarbonyl-D-diphenylalanyl-L-prolyl-[(5-amidino-2-thienyl)methyl]amide,
N-methoxycarbonyl-D-diphenylalanyl-L-prolyl-[(5-amidino-2-thienyl)methyl]amide,
N-aminosulfonyl-D-3,4-dichlorophenylalanyl-L-prolyl-[(5-amidino-2-thienyl)methyl]amide,
N-methoxycarbonyl-D-dicyclohexylalanyl-L-prolyl-[(5-amidino-2-thienyl)methyl]amide,
N-aminosulfonyl-D-diphenylalanyl -L- prolyl-[(4-amidino-2-thienyl) methyl]amide,
N-methylsulfonyl-D-diphenylalanyl-L-prolyl-[(4-amidino-2-thienyl)methyl]amide,
N-methylsulfonyl-D-diphenylalanyl-L-prolyl-[(4-aminomethyl-2-thienyl)methyl]amide,
N-methoxycarbonyl-D-diphenylalanyl-L-prolyl-[(4-amidino -2-thienyl) methyl]amide,
N-aminosulfonyl-D-diphenylalanyl-L-prolyl-[(5-amidino-3-thienyl)methyl]amide,
N-methylsulfonyl-D-diphenylalanyl-L-prolyl-[(5-amidino-3-thienyl)methyl]amide,
N-methylsulfonyl-D-diphenylalanyl-L-prolyl-[(5-amidrazono-3-thienyl)methyl]amide,
N-methylsulfonyl-D-diphenylalanyl-L-prolyl-[(5-aminomethyl-3-thienyl)methyl]amide,
N-methoxycarbonyl-D-diphenylalanyl-L-prolyl-[(5-amidino-3-thienyl)methyl]amide,
N-cyclohexylsulfamoyl-D-diphenylalanyl-L-prolyl-[(5-amidino-2-thienyl) methyl]amide,
N-allyloxycarbonyl-D-diphenylalanyl-L-prolyl-[(5-amidino-2-thienyl)methyl]amide,
N-benzylsulfonyl-D-cyclohexylalanyl-L-prolyl-[(5-amidino-2-thienyl)methyl]amide,
N-cyclohexylsulfamoyl-D-cyclohexylalanyl-L-prolyl-[(5-amidino-2-thienyl)methyl]amide,
N-methylsulfamoyl-D-cyclohexylalanyl-L-prolyl-[(5-amidino-2-thienyl)methyl]amide,
N-methylsulfonyl-D-cyclohexylglycinyl-L-prolyl-[(5-amidino -3-thienyl) methyl]amide,
N-carboxymethyl-D-diphenylalanyl-L-prolyl-[(5-amidino-2-thienyl)methyl]amide,
N-methyl-N-carboxymethyl-D-diphenylalanyl-L-prolyl-[(5-amidino-2-thienyl)methyl]amide,
N-hydroxysulfonyl-D-diphenylalanyl-L-prolyl-[(5-amidino-2-thienyl)methyl]amide,
N-methylsulfonyl-D-diphenylalanyl-L-prolyl-[(4-amidino -5-methyl-2-thienyl)methyl]amide,
N-methylsulfonyl-D-diphenylalanyl-L-prolyl-[(5-amidino-2-furanyl)methyl]amide,
N-methoxycabonyl-D-diphenylalanyl-L-prolyl-[(5-amidino-2-furanyl)methyl]amide,
N-aminosulfonyl-D-diphenylalanyl-L-prolyl-[(5-amidino-3-furanyl)methyl]amide,
N-aminosulfonyl-D-diphenylalanyl-L-prolyl-[(4-amidino-2-thiazolyl)methyl]amide,
N-methylsulfonyl-D-diphenylalanyl-L-prolyl-[(5-amidino-1-methyl-2-pyrrolyl)methyl]amide,
N-carboxymethyl-D-diphenylalanyl-L-prolyl-[(5-amidino-3-thienyl)methyl]amide,
N-carboxy methyl-D-diphenylalanyl-L-prolyl-[(4-amidino-2-thiazolyl) methyl]amide,
N-(2-carboxyethyl)-D-diphenylalanyl-L-prolyl-[(5-amidino-2-thienyl)methyl]amide,
N-Boc-D-Diphenylalanyl-L-prolyl-[(5-amidrazono-2-thienyl)methyl]amide,
D-diphenylalanyl-L-prolyl-[(5-amidrazono-2-thienyl)methyl]amide,
D-diphenylalanyl-L-prolyl-[(5-amidino-2-thienyl)methyl]amide,
N-(3-carboxypropyl)-D-diphenylalanyl-L-prolyl-[(5-amidino-2-thienyl)methyl]amide,
N-(MeO)$_2$P(O)-D-diphenylalanyl-L-prolyl-[(5-amidino-2-thienyl)methyl]amide,
N-(Me)$_2$P(O)-D-diphenylalanyl-L-prolyl-[(5-amidino-2-thienyl)methyl]amide,
N-(HO)$_2$P(O)-D-diphenylalanyl-L-prolyl-[(5-amidino-2-thienyl)methyl]amide,
N-methyl-D-diphenylalanyl-L-prolyl-[(5-amidino -2-thienyl)methyl]amide,
N-phenyl-D-diphenylalanyl-L-prolyl-[(5-amidino-2-thienyl)methyl]amide,
N-[(N,N-diethylcarboxamido)methyl]-D-diphenylalanyl-L-prolyl-[(5-amidino-2-thienyl)methyl]amide,
N-[(N,N-diethylcarboxamido)ethyl]-D-diphenylalanyl-L-prolyl-[(5-amidino-2-thienyl)methyl]amide,
N-aminosulfonyl-D-diphenylalanyl-L-prolyl-[(5-amidino-2-thiazolyl)methyl]amide,
N-aminosulfonyl-D-diphenylalanyl-L-prolyl-[(2-amidino-4-thiazolyl)methyl]amide,
N-aminosulfonyl-D-diphenylalanyl-L-prolyl-[(4-amidino-2-thiazolyl)methyl]amide, N-aminosulfonyl-D-diphenylalanyl-L-prolyl-[(2-amidino-5-thiazolyl)methyl]amide,
N-methylsulfonyl-D-diphenylalanyl-L-prolyl-[(5-amidino-2-thiazolyl)methyl]amide,
N-methylsulfonyl-D-diphenylalanyl-L-prolyl-[(2-amidino-4-thiazolyl) methyl]amide,
N-methylsulfonyl-D-diphenylalanyl-L-prolyl-[(4-amidino-2-thiazolyl)methyl]amide,
N-methylsulfonyl-D-diphenylalanyl-L-prolyl-[(2-amidino-5-thiazolyl)methyl]amide,
N-methoxycarbonyl-D-diphenylalanyl-L-prolyl-[(5-amidino-2-thiazolyl)methyl]amide,
N-methoxycarbonyl-D-diphenylalanyl-L-prolyl-[(2-amidino-4-thiazolyl)methyl]amide,
N-methoxycarbonyl-D-diphenylalanyl-L-prolyl-[(4-amidino-2-thiazolyl)methyl]amide,
N-methoxycarbonyl-D-diphenylalanyl-L-prolyl-[(2-amidino-5-thiazolyl)methyl]amide,
N-carboxymethyl-D-diphenylalanyl-L-prolyl-[(5-amidino-2-thiazolyl) methyl]amide,
N-carboxymethyl-D-diphenylalanyl-L-prolyl-[(2-amidino-4-thiazolyl)methyl]amide,
N-carboxymethyl-D-diphenylalanyl-L-prolyl-[(2-amidino-5-thiazolyl)methyl]amide,
N-aminosulfonyl-D-diphenylalanyl-L-prolyl-[(5-amidino-2-oxazolyl)methyl]amide,
N-aminosulfonyl-D-diphenylalanyl-L-prolyl-[(2-amidino-4-oxazolyl)methyl]amide,
N-aminosulfonyl-D-diphenylalanyl-L-prolyl-[(4-amidino-2-oxazolyl)methyl]amide,
N-aminosulfonyl-D-diphenylalanyl-L-prolyl-[(2-amidino-5-oxazolyl)methyl]amide,
N-methylsulfonyl-D-diphenylalanyl-L-prolyl-[(5-amidino-2-oxazolyl)methyl]amide,
N-methylsulfonyl-D-diphenylalanyl-L-prolyl-[(2-amidino-4-oxazolyl)methyl]amide,
N-methylsulfonyl-D-diphenylalanyl-L-prolyl-[(4-amidino-2-oxazolyl)methyl]amide,
N-methylsulfonyl-D-diphenylalanyl-L-prolyl-[(2-amidino-5-oxazolyl)methyl]amide,
N-methoxycarbonyl-D-diphenylalanyl-L-prolyl-[(5-amidino-2-oxazolyl)methyl]amide,
N-methoxycarbonyl-D-diphenylalanyl-L-prolyl-[(2-amidino-4-oxazolyl)methyl]amide,
N-methoxycarbonyl-D-diphenylalanyl-L-prolyl-[(4-amidino-2-oxazolyl)methyl]amide,
N-methoxycarbonyl-D-diphenylalanyl-L-prolyl-[(2-amidino-5-oxazolyl) methyl]amide,
N-carboxymethyl-D-diphenylalanyl-L-prolyl-[(5-amidino-2-oxazolyl)methyl]amide,
N-carboxymethyl-D-diphenylalanyl-L-prolyl-[(2-amidino-4-oxazolyl)methyl]amide,
N-carboxymethyl-D-diphenylalanyl-L-prolyl-[(4-amidino-2-oxazolyl)methyl]amide,
N-carboxymethyl-D-diphenylalanyl-L-prolyl-[(2-amidino-5-oxazolyl)methyl]amide,
N-aminosulfonyl-D-diphenylalanyl-L-prolyl-[(2-amidino-4-isoxazolyl)methyl]amide,
N-aminosulfonyl-D-diphenylalanyl-L-prolyl-[(4-amidino-2-isoxazolyl)methyl]amide,
N-methylsulfonyl-D-diphenylalanyl-L-prolyl-[(2-amidino-4-isoxazolyl)methyl]amide,
N-methylsulfonyl-D-diphenylalanyl-L-prolyl-[(4-amidino-2-isoxazolyl)methyl]amide,
N-methoxycarbonyl-D-diphenylalanyl-L-prolyl-[(2-amidino-4-isoxazolyl)methyl]amide,
N-methoxycarbonyl-D-diphenylalanyl-L-prolyl-[(4-amidino-2-isoxazolyl)methyl]amide,
N-carboxymethyl-D-diphenylalanyl-L-prolyl-[(4-amidino-2-isoxazolyl)methyl]amide,
N-carboxymethyl-D-diphenylalanyl-L-prolyl-[(2-amidino-4-isoxazolyl)methyl]amide,
N-aminosulfonyl-D-diphenylalanyl-L-prolyl-[(4-amidino-2-pyrazolyl)methyl]amide,
N-methylsulfonyl-D-diphenylalanyl-L-prolyl-[(4-amidino-2-pyrazolyl)methyl]amide,
N-methoxycarbonyl-D-diphenylalanyl-L-prolyl-[(4-amidino-2-pyrazolyl)methyl]amide,
N-carboxymethyl-D-diphenylalanyl-L-prolyl-[(4-amidino-2-pyrazolyl)methyl]amide,
N-aminosulfonyl-D-diphenylalanyl-L-prolyl-[(5-amidino-2-pyrrolyl)methyl]amide,
N-aminosulfonyl-D-diphenylalanyl-L-prolyl-[(4-amidino-2-pyrrolyl)methyl]amide,
N-aminosulfonyl-D-diphenylanyl-L-prolyl-[(5-amidino-3-pyrrolyl)methyl]amide,
N-methylsulfonyl-D-diphenylalanyl-L-prolyl-[(5-amidino-2-pyrrolyl)methyl]amide,
N-methylsulfonyl-D-diphenylalanyl-L-prolyl-[(4-amidino-2-pyrrolyl)methyl]amide,
N-methylsulfonyl-D-diphenylalanyl-L-prolyl-[(5-amidino-3-pyrrolyl)methyl]amide,
N-methoxycarbonyl-D-diphenylalanyl-L-prolyl-[(5-amidino-2-pyrrolyl)methyl]amide,
N-methoxycarbonyl-D-diphenylalanyl-L-prolyl-[(4-amidino-2-pyrrolyl)methyl]amide,
N-methoxycarbonyl-D-diphenylalanyl-L-prolyl-[(5-amidino-3-pyrrolyl)methyl]amide,
N-carboxymethyl-D-diphenylalanyl-L-prolyl-[(5-amidino-2-pyrrolyl)methyl]amide,
N-carboxymethyl-D-diphenylalanyl-L-prolyl-[(4-amidino-2-pyrrolyl)methyl]amide,
N-carboxymethyl-D-diphenylalanyl-L-prolyl-[(5-amidino-3-pyrrolyl)methyl]amide,
N-aminosulfonyl-D-bis-(para-methoxyphenyl)alanyl-L-prolyl-[(5-amidino-2-thienyl)methyl]amide,
N-methylsulfonyl-D-bis-(para-methoxyphenyl)alanyl-L-prolyl-[(5-amidino-2-thienyl)methyl]amide,
N-methoxycarbonyl-D-bis-(para-methoxyphenyl)alanyl-L-prolyl-[(5-amidino-2-thienyl)methyl]amide,
N-carboxymethyl-D-bis-(para-methoxyphenyl)alanyl-L-prolyl-[(5-amidino-2-thienyl)methyl]amide,
N-aminosulfonyl-D-bis-(para-aminophenyl)alanyl-L-prolyl-[(5-amidino-2-thienyl)methyl]amide,
N-methylsulfonyl-D-bis-(para-aminophenyl)alanyl-L-prolyl-[(5-amidino-2-thienyl)methyl]amide,
N-methoxycarbonyl-D-bis-(para-aminophenyl)alanyl-L-prolyl-[(5-amidino-2-thienyl)methyl]amide,
N-carboxymethyl-D-bis-(para-aminophenyl)alanyl-L-prolyl-[(5-amidino-2-thienyl)methyl]amide,
N-aminosulfonyl-D-bis-(para-chlorophenyl)alanyl-L-prolyl-[(5-amidino-2-thienyl)methyl]amide,
N-methylsulfonyl-D-bis-(para-chlorophenyl)alanyl-L-prolyl-[(5-amidino-2-thienyl)methyl]amide, N-methoxycarbonyl-D-bis-(para-chlorophenyl)alanyl-L-prolyl-[(5-amidino-2-thienyl)methyl]amide, and N-carboxymethyl-D-bis-(para-chlorophenyl)alanyl-L-prolyl-[(5-amidino-2-thienyl)methyl]amide, N-(t-butoxycarbonyl)methyl-D-diphenylalanyl-L-prolyl-[(5-amidino-2-thienyl)methyl]amide, N-(t-butoxycarbonyl)methyl-D-diphenylalanyl-L-prolyl-[(5-hydroxyamidino-2-thienyl)methyl]amide, N-[2-(methoxycarbonyl)ethyl]-D-diphenylalanyl-L-prolyl-[(5-amidino-2-thienyl)methyl]amide, N-carboxymethyl-D-diphenylalyl-L-prolyl-[(5-hydroxyamidino-2-thienyl)methyl]amide, N-(methoxycarbonyl)methyl-D-diphenylalanyl-L-prolyl-[(5-hydroxyamidino-2-thienyl)methyl]amide, N-aminosulfonyl-D-dicyclohexylalanyl-L-prolyl-[(5-amidino-2-thienyl)methyl]amide, N-methylsulfonyl-D-dicyclohexylalanyl-L-prolyl-[(5-amidino-2-thienyl)methyl]amide, N-carboxymethyl-D-dicyclohexylalanyl-L-prolyl-[(5-amidino-2-thienyl)methyl]amide;

and pharmaceutically acceptable salts thereof.

12. A method of modulating trypsin-like serine proteases comprising administering to a mammal in need of treatment for a cardiovascular disease an effective amount of the compound of claim 1.

13. A method of inhibiting trypsin-like serine proteases comprising administering to a mammal in need of treatment for a cardiovascular disease an effective amount of the compound of claim 1.

14. A method of modulating thrombin comprising administering to a mammal in need of treatment for a cardiovascular disease an effective amount of the compound of claim 1.

15. A method of inhibiting thrombin comprising administering to a mammal in need of treatment for a cardiovascular disease an effective amount of the compound of claim 1.

16. A method of any one of claims 12–15 whereby the cardiovascular disease is selected from the group consisting of myocardial infarction, unstable angina, deep vein thrombosis, and pulmonary embolism.

* * * * *